(12) United States Patent
Hong et al.

(10) Patent No.: US 11,708,357 B2
(45) Date of Patent: Jul. 25, 2023

(54) CRYSTAL FORM OF PYRROLIDINYL UREA DERIVATIVE AND APPLICATION THEREOF

(71) Applicant: ZHANGZHOU PIEN TZE HUANG PHARMACEUTICAL CO., LTD., Fujian (CN)

(72) Inventors: Fei Hong, Zhangzhou (CN); Zhiliang Chen, Zhangzhou (CN); Liju Wang, Zhangzhou (CN); Jinxia Lin, Zhangzhou (CN); Wenliang Lan, Zhangzhou (CN); Yang Zhang, Shanghai (CN); Wentao Wu, Shanghai (CN); Zhixiang Li, Shanghai (CN); Jian Qin, Shanghai (CN)

(73) Assignee: ZHANGZHOU PIEN TZE HUANG PHARMACEUTICAL CO., LTD., Fujian (CN)

( * ) Notice: Subject to any disclaimer, the term of this patent is extended or adjusted under 35 U.S.C. 154(b) by 0 days.

(21) Appl. No.: 17/791,694

(22) PCT Filed: Jan. 8, 2021

(86) PCT No.: PCT/CN2021/070956
§ 371 (c)(1),
(2) Date: Jul. 8, 2022

(87) PCT Pub. No.: WO2021/139794
PCT Pub. Date: Jul. 15, 2021

(65) Prior Publication Data
US 2023/0103409 A1    Apr. 6, 2023

(30) Foreign Application Priority Data
Jan. 10, 2020 (CN) .......................... 202010027389.4

(51) Int. Cl.
*C07D 405/14* (2006.01)

(52) U.S. Cl.
CPC ........ *C07D 405/14* (2013.01); *C07B 2200/13* (2013.01)

(58) Field of Classification Search
CPC ........ C07D 403/14; A61P 35/00; A61P 31/00; A61P 29/00; A61P 25/00; C07B 2200/13
See application file for complete search history.

(56) References Cited

U.S. PATENT DOCUMENTS

| | | |
|---|---|---|
| 9,878,997 B2 | 1/2018 | Allen et al. |
| 10,835,533 B2 | 11/2020 | Allen et al. |
| (Continued) | | |

FOREIGN PATENT DOCUMENTS

| | | |
|---|---|---|
| CN | 103649076 A | 3/2014 |
| CN | 106459013 A | 2/2017 |
| (Continued) | | |

OTHER PUBLICATIONS

Jan. 31, 2023 Japanese First Office Action issued in Japanese Patent Application No. 2022542633.
International Search Report (English and Chinese) issued in PCT/CN2021/070956, dated Apr. 16, 2021; ISA/CN.
Written Opinion of the International Searching Authority (English and Chinese) issued in PCT/CN2021/070956, dated Apr. 16, 2021; ISA/CN.

*Primary Examiner* — Kortney L. Klinkel
*Assistant Examiner* — Padmaja S Rao
(74) *Attorney, Agent, or Firm* — Harness, Dickey & Pierce, P.L.C.

(57) ABSTRACT

Disclosed in the present invention are a crystal form of a TrkA inhibitor and a preparation method thereof, and an application thereof in preparation of drugs for treating diseases associated with pain, cancer, inflammation, neurodegenerative diseases, and certain infectious diseases.

(Continued)

(56) References Cited

U.S. PATENT DOCUMENTS

| | | | |
|---|---|---|---|
| 2017/0240512 A1 | 8/2017 | Yukimasa et al. |
| 2018/0201607 A1 | 7/2018 | Yukimasa et al. |
| 2019/0359597 A1 | 11/2019 | Allen et al. |
| 2021/0147436 A1 | 5/2021 | Zhang et al. |

FOREIGN PATENT DOCUMENTS

| | | | |
|---|---|---|---|
| JP | 2014514360 A | 6/2014 | |
| JP | 2017518981 A | 7/2017 | |
| JP | 7083436 B2 | 6/2022 | |
| WO | 2012158413 A2 | 11/2012 | |
| WO | 2015175788 A1 | 11/2015 | |
| WO | 2016021629 A1 | 2/2016 | |
| WO | 2016116900 A1 | 7/2016 | |
| WO | 2017006953 A1 | 1/2017 | |
| WO | WO-2020011227 A1 * | 1/2020 | ............. A61P 25/00 |

\* cited by examiner

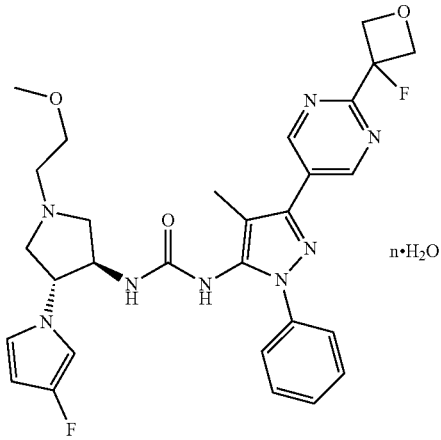

15 Claims, 10 Drawing Sheets

CRYSTAL FORM OF PYRROLIDINYL UREA DERIVATIVE AND APPLICATION THEREOF

CROSS-REFERENCE TO RELATED APPLICATIONS

This application is a U.S. National Phase Application under 35 U.S.C. 371 of International Application No. PCT/CN2021/070956, filed on Jan. 8, 2021, which claims the benefit of Chinese Patent Application No. 202010027389.4, filed on Jan. 10, 2020. The entire disclosures of the above applications are incorporated herein by reference.

TECHNICAL FIELD

The present disclosure relates to a crystal form of a TrkA inhibitor and a preparation method therefor, and use thereof in the manufacture of medicaments for treating diseases associated with pain, cancer, inflammation, neurodegenerative diseases, and certain infectious diseases.

BACKGROUND

Tropomyosin-related kinase (Trk) is a high-affinity receptor tyrosine kinase activated by a group of soluble growth factors called nerve growth factor (NGF), brain-derived neurotrophic factor (BDNF) and neurotrophic factor (NT). The family of the Trk consists of three members (TrkA, TrkB and TrkC). NGF, BDNF and NT-4/5 play an important role in many physiological regulation processes such as neuronal cell signal maintenance, neuronal cell signal transmission, cell proliferation, cell differentiation, and cell survival through a receptor Trk. There is a lot of evidence that inhibitors of NGF/Trk signaling pathway are effective in many preclinical models of pain; and the inhibitors of NGF/Trk signaling pathway are effective in many preclinical models of inflammatory diseases. Furthermore, overexpression, activation, amplification and/or mutation of Trk kinases are associated with many tumors or cancers. Therefore, Trk has emerged as an important class of therapeutic targets that has attracted extensive research and development interest. The TrkA inhibitors of the present disclosure can meet the treatment requirements of pain, cancer, inflammation, neurodegenerative diseases and certain infectious diseases.

WO2015175788 patent reported a single compound with inhibitory activity against TrkA and a pharmaceutically acceptable salt thereof. WO2012158413, WO2016116900, WO2016021629, WO2017006953 patents reported a series of compounds with inhibitory activity against TrkA, including a pyrrolidinyl urea structure used in the present disclosure.

CONTENT OF THE PRESENT INVENTION

The present disclosure provides a crystal form A of a compound of formula (I), which is characterized in that the X-ray powder diffraction pattern thereof comprises characteristic diffraction peaks at the following angles of 2θ: 13.40±0.20°, 18.71±0.20° and 19.51±0.20°.

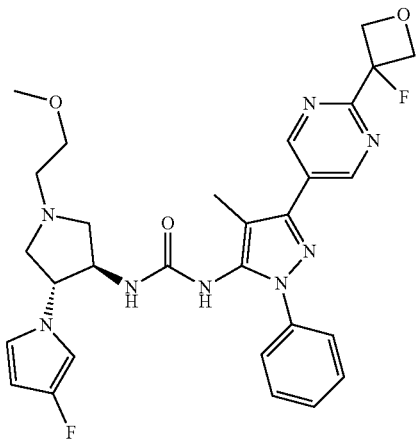

(I)

In some embodiments of the present disclosure, the X-ray powder diffraction pattern of the crystal form A comprises characteristic diffraction peaks at the following angles of 2θ: 9.34±0.20°, 13.40±0.20°, 14.57±0.20°, 15.59±0.20°, 16.95±0.20°, 18.71±0.20°, 19.51±0.20° and 24.07±0.20°.

In some embodiments of the present disclosure, the X-ray powder diffraction pattern of the crystal form A comprises characteristic diffraction peaks at the following angles of 2θ: 6.06°, 8.30°, 9.05°, 9.34°, 10.52°, 11.86°, 12.34°, 13.40°, 14.25°, 14.57°, 15.30°, 15.59°, 16.95°, 17.74°, 18.45°, 18.71°, 19.51°, 19.88°, 20.33°, 21.03°, 21.60°, 22.61°, 23.64°, 24.07°, 24.53°, 25.37°, 26.41°, 27.05°, 27.74°, 28.10°, 30.48°, 34.72°, 36.84° and 37.60°.

In some embodiments of the present disclosure, the X-ray powder diffraction (XRPD) pattern of the crystal form A is shown in FIG. 1.

In some embodiments of the present disclosure, the analytical data of the XRPD pattern of the crystal form A are shown in Table 1:

TABLE 1

Analytical data of the XRPD pattern of the crystal form A

| No. | Angle of 2θ (°) | d-Spacing (Å) | Relative intensity (%) |
|---|---|---|---|
| 1 | 6.06 | 14.58 | 33.12 |
| 2 | 8.30 | 10.65 | 7.92 |
| 3 | 9.05 | 9.78 | 26.57 |
| 4 | 9.34 | 9.47 | 58.88 |
| 5 | 10.52 | 8.41 | 9.55 |
| 6 | 11.86 | 7.46 | 21.73 |
| 7 | 12.34 | 7.17 | 39.29 |
| 8 | 13.40 | 6.61 | 68.59 |
| 9 | 14.25 | 6.22 | 22.79 |
| 10 | 14.57 | 6.08 | 58.86 |
| 11 | 15.30 | 5.79 | 43.01 |
| 12 | 15.59 | 5.68 | 59.07 |
| 13 | 16.95 | 5.23 | 63.76 |
| 14 | 17.74 | 5.00 | 42.93 |
| 15 | 18.45 | 4.81 | 51.28 |
| 16 | 18.71 | 4.74 | 100.00 |
| 17 | 19.51 | 4.55 | 77.74 |
| 18 | 19.88 | 4.47 | 67.15 |
| 19 | 20.33 | 4.37 | 32.68 |
| 20 | 21.03 | 4.22 | 37.49 |
| 21 | 21.60 | 4.11 | 28.42 |
| 22 | 22.61 | 3.93 | 21.07 |
| 23 | 23.64 | 3.76 | 35.78 |
| 24 | 24.07 | 3.70 | 62.33 |

TABLE 1-continued

Analytical data of the XRPD pattern of the crystal form A

| No. | Angle of 2θ (°) | d-Spacing (Å) | Relative intensity (%) |
|---|---|---|---|
| 25 | 24.53 | 3.63 | 23.59 |
| 26 | 25.37 | 3.51 | 22.21 |
| 27 | 26.41 | 3.37 | 17.99 |
| 28 | 27.05 | 3.30 | 11.64 |
| 29 | 27.74 | 3.22 | 13.07 |
| 30 | 28.10 | 3.18 | 13.22 |
| 31 | 30.48 | 2.93 | 9.77 |
| 32 | 34.72 | 2.58 | 8.59 |
| 33 | 36.84 | 2.44 | 1.77 |
| 34 | 37.60 | 2.39 | 2.46 |

In some embodiments of the present disclosure, the differential scanning calorimetry curve of the crystal form A has an endothermic peak at 75.3±3.0° C., 99.6±3.0° C. and 167.9±3.0° C. respectively and an exothermic peak at 132.3±3.0° C.

In some embodiments of the present disclosure, the DSC pattern of the crystal form A is shown in FIG. 2.

In some embodiments of the present disclosure, the thermogravimetric analysis curve of the crystal form A shows a weight loss of 1.75% occurred at 55.0±3.0° C., and a weight loss of 3.08% occurred at 100.0±3.0° C.

In some embodiments of the present disclosure, the TGA pattern of the crystal form A is shown in FIG. 3.

The present disclosure also provides a crystal form B of the compound of formula (I), which is characterized in that the X-ray powder diffraction pattern thereof comprises characteristic diffraction peaks at the following angles of 2θ: 9.56±0.20°, 14.80±0.20° and 19.33±0.20°.

In some embodiments of the present disclosure, the X-ray powder diffraction pattern of the crystal form B comprises characteristic diffraction peaks at the following angles of 2θ: 4.94±0.20°, 9.56±0.20°, 10.76±0.20°, 12.09±0.20°, 14.80±0.20°, 19.33±0.20°, 20.56±0.20° and 21.60±0.20°.

In some embodiments of the present disclosure, the X-ray powder diffraction pattern of the crystal form B comprises characteristic diffraction peaks at the following angles of 2θ: 4.94°, 9.56°, 9.86°, 10.76°, 12.09°, 13.73°, 14.80°, 15.59°, 17.63°, 19.33°, 19.79°, 20.56°, 21.60°, 21.98°, 22.84°, 23.86°, 24.29°, 24.77°, 26.61°, 27.65°, 28.97°, 29.83°, 30.62°, 31.51°, 34.92°, 38.93° and 39.61°.

In some embodiments of the present disclosure, the XRPD pattern of the crystal form B is shown in FIG. 4.

In some embodiments of the present disclosure, the analytical data of the XRPD pattern of the crystal form B are shown in Table 2:

TABLE 2

Analytical data of the XRPD pattern of the crystal form B

| No. | Angle of 2θ (°) | d-Spacing (Å) | Relative intensity (%) |
|---|---|---|---|
| 1 | 4.94 | 17.89 | 2.30 |
| 2 | 9.56 | 9.25 | 100.00 |
| 3 | 9.86 | 8.97 | 3.06 |
| 4 | 10.76 | 8.22 | 3.40 |
| 5 | 12.09 | 7.32 | 5.92 |
| 6 | 13.73 | 6.45 | 1.02 |
| 7 | 14.80 | 5.99 | 6.96 |
| 8 | 15.59 | 5.68 | 0.82 |
| 9 | 17.63 | 5.03 | 0.96 |

TABLE 2-continued

Analytical data of the XRPD pattern of the crystal form B

| No. | Angle of 2θ (°) | d-Spacing (Å) | Relative intensity (%) |
|---|---|---|---|
| 10 | 19.33 | 4.59 | 23.86 |
| 11 | 19.79 | 4.49 | 11.99 |
| 12 | 20.56 | 4.32 | 5.45 |
| 13 | 21.60 | 4.11 | 1.33 |
| 14 | 21.98 | 4.04 | 0.60 |
| 15 | 22.84 | 3.89 | 1.27 |
| 16 | 23.86 | 3.73 | 0.40 |
| 17 | 24.29 | 3.66 | 0.90 |
| 18 | 24.77 | 3.59 | 1.56 |
| 19 | 26.61 | 3.35 | 0.29 |
| 20 | 27.65 | 3.23 | 0.27 |
| 21 | 28.97 | 3.08 | 0.82 |
| 22 | 29.83 | 3.00 | 0.73 |
| 23 | 30.62 | 2.92 | 0.38 |
| 24 | 31.51 | 2.84 | 0.59 |
| 25 | 34.92 | 2.57 | 0.80 |
| 26 | 38.93 | 2.31 | 0.59 |
| 27 | 39.61 | 2.28 | 0.55 |

In some embodiments of the present disclosure, the differential scanning calorimetry curve of the crystal form B has an endothermic peak at 99.6±3.0° C., 159.5±3.0° C. and 172.9±3.0° C., respectively.

In some embodiments of the present disclosure, the DSC pattern of the crystal form B is shown in FIG. 5.

In some embodiments of the present disclosure, the thermogravimetric analysis curve of the crystal form B has a weight loss of 5.96% occurred at 130.0±3.0° C.

In some embodiments of the present disclosure, the TGA pattern of the crystal form B is shown in FIG. 6.

The present disclosure also provides a crystal form C of the compound of formula (I), which is characterized in that the X-ray powder diffraction pattern thereof comprises characteristic diffraction peaks at the following angles of 2θ: 9.55°±0.20°, 12.07°±0.20° and 19.32°±0.20°.

In some embodiments of the present disclosure, the X-ray powder diffraction pattern of the crystal form C comprises characteristic diffraction peaks at the following angles of 2θ: 4.88±0.20°, 9.55±0.20°, 10.73±0.20°, 12.07±0.20°, 14.77±0.20°, 19.32±0.20°, 20.55±0.20° and 22.80±0.20°.

In some embodiments of the present disclosure, the X-ray powder diffraction pattern of the crystal form C comprises characteristic diffraction peaks at the following angles of 2θ: 4.88°, 9.55°, 9.84°, 10.73°, 12.07°, 14.37°, 14.77°, 15.58°, 19.32°, 19.76°, 20.55°, 22.80°, 23.09°, 23.89°, 24.72°, 25.83° and 28.58°.

In some embodiments of the present disclosure, the XRPD pattern of the crystal form C is shown in FIG. 7.

In some embodiments of the present disclosure, the analytical data of the XRPD pattern of the crystal form C are shown in Table 3:

TABLE 3

Analytical data of the XRPD pattern of the crystal form C

| No. | Angle of 2θ (°) | d-Spacing (Å) | Relative intensity (%) |
|---|---|---|---|
| 1 | 4.88 | 18.10 | 5.87 |
| 2 | 9.55 | 9.26 | 100.00 |
| 3 | 9.84 | 8.99 | 6.78 |
| 4 | 10.73 | 8.25 | 7.60 |

TABLE 3-continued

Analytical data of the XRPD pattern of the crystal form C

| No. | Angle of 2θ (°) | d-Spacing (Å) | Relative intensity (%) |
|---|---|---|---|
| 5 | 12.07 | 7.33 | 12.08 |
| 6 | 14.37 | 6.16 | 5.11 |
| 7 | 14.77 | 6.00 | 12.50 |
| 8 | 15.58 | 5.69 | 3.06 |
| 9 | 19.32 | 4.59 | 23.84 |
| 10 | 19.76 | 4.49 | 17.86 |
| 11 | 20.55 | 4.32 | 9.92 |
| 12 | 22.80 | 3.90 | 5.20 |
| 13 | 23.09 | 3.85 | 4.57 |
| 14 | 23.89 | 3.73 | 4.06 |
| 15 | 24.72 | 3.60 | 4.66 |
| 16 | 25.83 | 3.45 | 1.94 |
| 17 | 28.58 | 3.12 | 1.91 |

In some embodiments of the present disclosure, the differential scanning calorimetry curve of the crystal form C has an endothermic peak at 90.0±3.0° C., 156.2±3.0° C. and 175.0±3.0° C. respectively and an exothermic peak at 98.3±3.0° C.

In some embodiments of the present disclosure, the DSC pattern of the crystal form C is shown in FIG. 8.

In some embodiments of the present disclosure, the thermogravimetric analysis curve of the crystal form C has a weight loss of 4.68% occurred at 70.0±3.0° C., and a weight loss of 5.38% occurred at 100.0±3.0° C.

In some embodiments of the present disclosure, the TGA pattern of the crystal form C is shown in FIG. 9.

The present disclosure also provides a crystal form D of the compound of formula (I), which is characterized in that the X-ray powder diffraction pattern thereof comprises characteristic diffraction peaks at the following angles of 2θ: 9.53°±0.20°, 19.33°±0.20° and 20.56°±0.20°.

In some embodiments of the present disclosure, the X-ray powder diffraction pattern of the crystal form D comprises characteristic diffraction peaks at the following angles of 2θ: 9.53±0.20°, 10.76±0.20°, 12.09±0.20°, 14.81±0.20°, 18.86±0.20°, 19.33±0.20°, 20.56±0.20° and 22.83±0.20°.

In some embodiments of the present disclosure, the X-ray powder diffraction pattern of the crystal form D comprises characteristic diffraction peaks at the following angles of 2θ: 4.96°, 9.53°, 10.76°, 12.09°, 13.72°, 14.81°, 15.61°, 17.55°, 18.86°, 19.33°, 19.79°, 20.56°, 21.53°, 22.83°, 24.29°, 24.77°, 27.65°, 28.94°, 29.86°, 30.61°, 31.51°, 38.91° and 39.60°.

In some embodiments of the present disclosure, the XRPD pattern of the crystal form D is shown in FIG. 10.

In some embodiments of the present disclosure, the analytical data of the XRPD pattern of the crystal form D are shown in Table 4:

TABLE 4

Analytical data of the XRPD pattern of the crystal form D

| No. | Angle of 2θ (°) | d-Spacing (Å) | Relative intensity (%) |
|---|---|---|---|
| 1 | 4.96 | 17.82 | 2.19 |
| 2 | 9.53 | 9.28 | 100.00 |
| 3 | 10.76 | 8.22 | 7.61 |
| 4 | 12.09 | 7.32 | 9.79 |
| 5 | 13.72 | 6.45 | 1.49 |
| 6 | 14.81 | 5.98 | 3.80 |

TABLE 4-continued

Analytical data of the XRPD pattern of the crystal form D

| No. | Angle of 2θ (°) | d-Spacing (Å) | Relative intensity (%) |
|---|---|---|---|
| 7 | 15.61 | 5.68 | 1.78 |
| 8 | 17.55 | 5.05 | 0.89 |
| 9 | 18.86 | 4.71 | 14.63 |
| 10 | 19.33 | 4.59 | 35.36 |
| 11 | 19.79 | 4.49 | 23.14 |
| 12 | 20.56 | 4.32 | 14.22 |
| 13 | 21.53 | 4.13 | 1.96 |
| 14 | 22.83 | 3.89 | 4.06 |
| 15 | 24.29 | 3.66 | 1.99 |
| 16 | 24.77 | 3.59 | 0.97 |
| 17 | 27.65 | 3.23 | 0.39 |
| 18 | 28.94 | 3.09 | 1.41 |
| 19 | 29.86 | 2.99 | 1.01 |
| 20 | 30.61 | 2.92 | 1.05 |
| 21 | 31.51 | 2.84 | 1.36 |
| 22 | 38.91 | 2.31 | 0.88 |
| 23 | 39.60 | 2.28 | 0.73 |

In some embodiments of the present disclosure, the differential scanning calorimetry curve of the crystal form D has an endothermic peak at 89.2±3.0° C., 157.6±3.0° C. and 162.7±3.0° C. respectively and an exothermic peak at 127.1±3.0° C.

In some embodiments of the present disclosure, the DSC pattern of the crystal form D is shown in FIG. 11.

In some embodiments of the present disclosure, the thermogravimetric analysis curve of the crystal form D has a weight loss of 5.13% occurred at 130.0±3.0° C.

In some embodiments of the present disclosure, the TGA pattern of the crystal form D is shown in FIG. 12.

The present disclosure also provides a crystal form E of a compound of formula (II), which is characterized in that the X-ray powder diffraction pattern thereof comprises characteristic diffraction peaks at the following angles of 2θ: 9.56°±0.20°, 12.08°±0.20° and 19.29°±0.20°, wherein, n is 0 or 2.

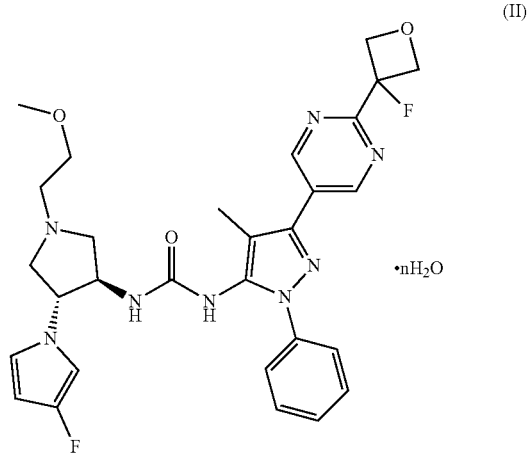

(II)

·nH$_2$O

The present disclosure also provides a crystal form E of the compound of formula (I), which is characterized in that the X-ray powder diffraction pattern thereof has characteristic diffraction peaks at the following angles of 2θ: 9.56°±0.20°, 12.08°±0.20° and 19.29°±0.20°.

In some embodiments of the present disclosure, the X-ray powder diffraction pattern of the crystal form E comprises characteristic diffraction peaks at the following angles of 2θ: 9.56±0.20°, 10.75±0.20°, 12.08±0.20°, 14.78±0.20°, 15.60±0.20°, 19.29±0.20°, 20.55±0.20° and 22.82±0.20°.

In some embodiments of the present disclosure, the X-ray powder diffraction pattern of the crystal form E comprises characteristic diffraction peaks at the following angles of 2θ: 4.91°, 9.56°, 10.75°, 12.08°, 13.70°, 14.78°, 15.60°, 17.62°, 19.29°, 19.78°, 20.55°, 21.58°, 22.82°, 23.85°, 24.29°, 24.74°, 25.86°, 26.59°, 27.70°, 28.56°, 28.94°, 30.67°, 31.50° and 37.80°.

In some embodiments of the present disclosure, the XRPD pattern of the crystal form E is shown in FIG. 13.

In some embodiments of the present disclosure, the analytical data of the XRPD pattern of the crystal form E are shown in Table 5:

TABLE 5

Analytical data of the XRPD pattern of the crystal form E

| No. | Angle of 2θ (°) | d-Spacing (Å) | Relative intensity (%) |
|---|---|---|---|
| 1 | 4.91 | 18.02 | 1.52 |
| 2 | 9.56 | 9.25 | 100.00 |
| 3 | 10.75 | 8.23 | 6.86 |
| 4 | 12.08 | 7.33 | 12.84 |
| 5 | 13.70 | 6.46 | 2.05 |
| 6 | 14.78 | 5.99 | 4.60 |
| 7 | 15.60 | 5.68 | 3.25 |
| 8 | 17.62 | 5.03 | 2.61 |
| 9 | 19.29 | 4.60 | 17.07 |
| 10 | 19.78 | 4.49 | 16.73 |
| 11 | 20.55 | 4.32 | 12.01 |
| 12 | 21.58 | 4.12 | 2.50 |
| 13 | 22.82 | 3.90 | 4.00 |
| 14 | 23.85 | 3.73 | 2.71 |
| 15 | 24.29 | 3.66 | 2.09 |
| 16 | 24.74 | 3.60 | 2.74 |
| 17 | 25.86 | 3.45 | 1.43 |
| 18 | 26.59 | 3.35 | 0.67 |
| 19 | 27.70 | 3.22 | 0.73 |
| 20 | 28.56 | 3.13 | 1.04 |
| 21 | 28.94 | 3.09 | 0.86 |
| 22 | 30.67 | 2.92 | 1.45 |
| 23 | 31.50 | 2.84 | 1.45 |
| 24 | 37.80 | 2.38 | 0.38 |

In some embodiments of the present disclosure, the differential scanning calorimetry curve of the crystal form E has an endothermic peak at 94.0±3.0° C., 154.0±3.0° C. and 171.7±3.0° C. respectively and an exothermic peak at 123.8±3.0° C.

In some embodiments of the present disclosure, the DSC pattern of the crystal form E is shown in FIG. 14.

In some embodiments of the present disclosure, the thermogravimetric analysis curve of the crystal form E has a weight loss of 5.84% occurred at 130.0±3.0° C.

In some embodiments of the present disclosure, the TGA pattern of the crystal form E is shown in FIG. 15.

The present disclosure also provides a crystal form F of a compound of formula (IV), which is characterized in that the X-ray powder diffraction pattern thereof comprises characteristic diffraction peaks at the following angles of 2θ: 6.30°±0.20°, 13.62°±0.20° and 18.92°±0.20°.

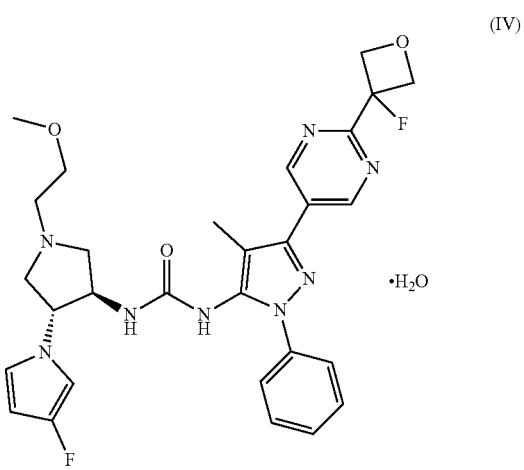 [SMILES: COCCN1C[C@@H](n2ccc(F)c2)[C@H](NC(=O)Nc2c(C)c(-c3cnc(C4(F)COC4)nc3)nn2-c2ccccc2)C1 ; O]

(IV)

The present disclosure also provides a crystal form F of the compound of formula (I), which is characterized in that the X-ray powder diffraction pattern thereof comprises characteristic diffraction peaks at the following angles of 2θ: 6.30°±0.20°, 13.62°±0.20° and 18.92°±0.20°.

In some embodiments of the present disclosure, the X-ray powder diffraction pattern of the crystal form F comprises characteristic diffraction peaks at the following angles of 2θ: 6.30±0.20°, 9.25±0.20°, 13.62±0.20°, 15.80±0.20°, 17.16±0.20°, 17.96±0.20°, 18.92±0.20° and 20.09±0.20°.

In some embodiments of the present disclosure, the X-ray powder diffraction pattern of the crystal form F comprises characteristic diffraction peaks at the following angles of 2θ: 6.30°, 8.48°, 9.25°, 9.71°, 12.57°, 13.62°, 14.46°, 15.80°, 17.16°, 17.96°, 18.67°, 18.92°, 19.69°, 20.09°, 21.26°, 22.15°, 23.68°, 24.29°, 25.58°, 26.64°, 27.32°, 27.95°, 28.28°, 30.71° and 35.16°.

In some embodiments of the present disclosure, the XRPD pattern of the crystal form F is shown in FIG. 16.

In some embodiments of the present disclosure, the analytical data of the XRPD pattern of the crystal form F are as shown in Table 6:

TABLE 6

Analytical data of the XRPD pattern of the crystal form F

| No. | Angle of 2θ (°) | d-Spacing (Å) | Relative intensity (%) |
|---|---|---|---|
| 1 | 6.30 | 14.03 | 91.49 |
| 2 | 8.48 | 10.42 | 8.60 |
| 3 | 9.25 | 9.56 | 34.79 |
| 4 | 9.71 | 9.11 | 20.06 |
| 5 | 12.57 | 7.04 | 22.85 |
| 6 | 13.62 | 6.50 | 82.23 |
| 7 | 14.46 | 6.12 | 6.86 |
| 8 | 15.80 | 5.61 | 53.42 |
| 9 | 17.16 | 5.17 | 33.80 |
| 10 | 17.96 | 4.94 | 23.14 |
| 11 | 18.67 | 4.75 | 32.43 |
| 12 | 18.92 | 4.69 | 100.00 |
| 13 | 19.69 | 4.51 | 19.93 |
| 14 | 20.09 | 4.42 | 41.85 |
| 15 | 21.26 | 4.18 | 19.87 |

TABLE 6-continued

Analytical data of the XRPD pattern of the crystal form F

| No. | Angle of 2θ (°) | d-Spacing (Å) | Relative intensity (%) |
|---|---|---|---|
| 16 | 22.15 | 4.01 | 3.96 |
| 17 | 23.68 | 3.76 | 3.80 |
| 18 | 24.29 | 3.66 | 20.99 |
| 19 | 25.58 | 3.48 | 15.86 |
| 20 | 26.64 | 3.35 | 8.72 |
| 21 | 27.32 | 3.26 | 4.44 |
| 22 | 27.95 | 3.19 | 12.93 |
| 23 | 28.28 | 3.16 | 12.80 |
| 24 | 30.71 | 2.91 | 4.81 |
| 25 | 35.16 | 2.55 | 1.90 |

In some embodiments of the present disclosure, the differential scanning calorimetry curve of the crystal form F has an endothermic peak at 100.0±3.0° C. and 172.7±3.0° C. respectively and an exothermic peak at 126.0±3.0° C.

In some embodiments of the present disclosure, the DSC pattern of the crystal form F is shown in FIG. 17.

In some embodiments of the present disclosure, the thermogravimetric analysis curve of the crystal form F has a weight loss of 3.92% occurred at 130.0±3.0° C.

In some embodiments of the present disclosure, the TGA pattern of the crystal form F is shown in FIG. 18.

The present disclosure also provides a preparation method for the crystal form E of the compound of formula (I), comprising adding any form of the compound of formula (I) into an alcohol solvent, a mixed solvent of the alcohol solvent and water, or a mixed solvent of acetonitrile and water, stirring at a certain temperature for a certain time, then centrifuging, and drying a residue to obtain the crystal form E of the compound of formula (I).

In some embodiments of the present disclosure, the alcohol solvent is selected from methanol and ethanol.

In some embodiments of the present disclosure, the volume ratio of the alcohol solvent to water or acetonitrile to water is selected from 1:1 to 4.

In some embodiments of the present disclosure, a temperature for the stirring is selected from 20° C. to 60° C.

In some embodiments of the present disclosure, a time for the stirring is selected from 48 hours to 96 hours.

In some embodiments of the present disclosure, the weight-to-volume (mg/mL) ratio of the compound of formula (I) to the solvent is selected from 10 to 100:1.

The present disclosure also provides a crystal of the compound of formula (II), which is characterized in that the X-ray powder diffraction pattern thereof comprises characteristic diffraction peaks at the following angles of 2θ: 9.56±0.40°, 12.08±0.40° and 19.29±0.40°, wherein, n is 0 or 2.

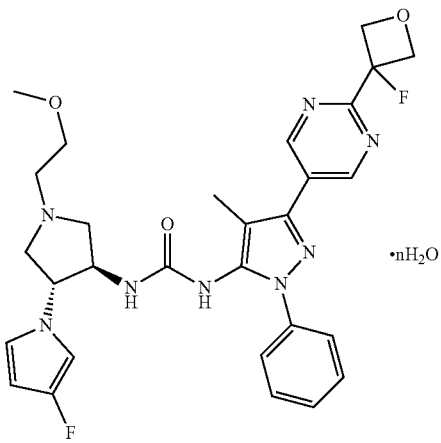 [SMILES: COCCN1C[C@@H](n2ccc(F)c2)[C@H](NC(=O)Nc2c(C)c(-c3cnc(C4(F)COC4)nc3)nn2-c2ccccc2)C1]

In some embodiments of the present disclosure, the X-ray powder diffraction pattern of the crystal of the compound of formula (II) comprises characteristic diffraction peaks at the following angles of 2θ: 9.56±0.40°, 12.08±0.40°, 19.29±0.40° and 20.55±0.40°.

In some embodiments of the present disclosure, the X-ray powder diffraction pattern of the crystal of the compound of formula (II) comprises characteristic diffraction peaks at the following angles of 2θ: 9.56±0.40°, 10.75±0.40°, 12.08±0.40°, 14.78±0.40°, 19.29±0.40° and 20.55±0.40°.

In some embodiments of the present disclosure, the X-ray powder diffraction pattern of the crystal of the compound of formula (II) comprises characteristic diffraction peaks at the following angles of 2θ: 9.56±0.40°, 10.75±0.40°, 12.08±0.40°, 14.78±0.40°, 19.29±0.40°, 20.55±0.40°, 22.82±0.40° and 24.74±0.40°.

In some embodiments of the present disclosure, the crystal of the compound of formula (II) is selected from the crystal form B, the crystal form C, the crystal form D and the crystal form E.

The present disclosure also provides the crystal of the compound of formula (II), wherein the compound of formula (II) has the following structure.

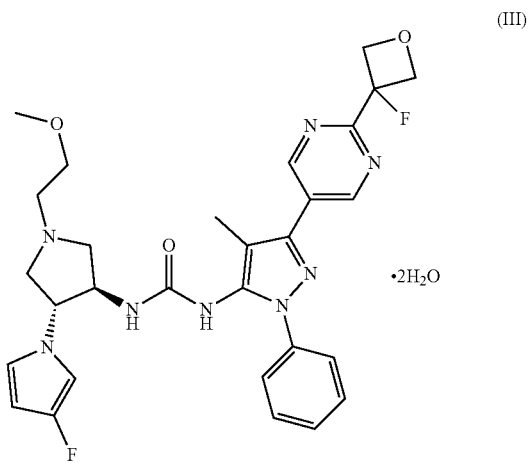 [SMILES: COCCN1C[C@@H](n2ccc(F)c2)[C@H](NC(=O)Nc2c(C)c(-c3cnc(C4(F)COC4)nc3)nn2-c2ccccc2)C1]

(III)

In some embodiments of the present disclosure, the crystal of the compound of formula (II) is characterized in that the X-ray powder diffraction pattern thereof comprises characteristic diffraction peaks at the following angles of 2θ: 9.3138°±0.2000°, 19.0764°±0.2000° and 19.5885°±0.2000°.

In some embodiments of the present disclosure, the X-ray powder diffraction pattern of the crystal of the compound of formula (II) comprises characteristic diffraction peaks at the following angles of 2θ: 9.3138°±0.2000°, 10.515°±0.2000°, 11.9125°±0.2000°, 19.0764°±0.2000°, 19.5885°±0.2000° and 22.7144°±0.2000°.

In some embodiments of the present disclosure, the X-ray powder diffraction pattern of the crystal of the compound of formula (II) comprises characteristic diffraction peaks at the following angles of 2θ: 9.3138°±0.2000°, 10.515°±0.2000°, 11.9125°±0.2000°, 14.5999°±0.2000°, 19.0764°±0.2000°, 19.5885°±0.2000°, 20.2743°±0.2000°, 21.3180°±0.2000°, 22.7144°±0.20° and 24.5829°±0.20°.

In some embodiments of the present disclosure, the X-ray powder diffraction pattern of the crystal of the compound of formula (II) comprises characteristic diffraction peaks at the following angles of 2θ: 9.0233°, 9.3138°, 9.4821°, 10.5145°, 10.7290°, 11.9125°, 14.5999°, 18.9000°, 19.0764°, 19.2297°, 19.5885°, 19.7576°, 20.2743°, 20.4715°, 21.3180°, 21.5603°, 22.7144°, 23.6499° and 24.5829°.

In some embodiments of the present disclosure, the XRPD pattern of the crystal of the compound of formula (II) is shown in FIG. 20.

In some embodiments of the present disclosure, the analytical data of the XRPD pattern of the crystal of the compound of formula (II) are shown in Table 15:

TABLE 15

Analytical data of the XRPD pattern of the crystal of the compound of formula (II)

| No. | Angle of 2θ (°) | Intensity (count) | d-Spacing (Å) | Relative intensity (%) |
|---|---|---|---|---|
| 1 | 4.7266 | 424.8400 | 18.69578 | 0.96 |
| 2 | 9.0233 | 2509.0200 | 9.80065 | 5.69 |
| 3 | 9.3138 | 44126.8100 | 9.49565 | 100.00 |
| 4 | 9.4821 | 15283.0000 | 9.32740 | 34.63 |
| 5 | 10.5145 | 2861.0500 | 8.41379 | 6.48 |
| 6 | 10.7290 | 1141.7100 | 8.24610 | 2.59 |
| 7 | 11.9125 | 2100.4400 | 7.42935 | 4.76 |
| 8 | 13.5672 | 463.7100 | 6.52675 | 1.05 |
| 9 | 14.5999 | 1187.1100 | 6.06731 | 2.69 |
| 10 | 15.3967 | 643.1700 | 5.75509 | 1.46 |
| 11 | 17.4253 | 259.3700 | 5.08939 | 0.59 |
| 12 | 18.9000 | 4219.3700 | 4.69549 | 9.56 |
| 13 | 19.0764 | 10750.3500 | 4.65246 | 24.36 |
| 14 | 19.2297 | 6694.2400 | 4.61572 | 15.17 |
| 15 | 19.5885 | 5985.9800 | 4.53197 | 13.57 |
| 16 | 19.7576 | 3293.2400 | 4.49356 | 7.46 |
| 17 | 20.2743 | 1776.6600 | 4.38019 | 4.03 |
| 18 | 20.4715 | 1508.6300 | 4.33845 | 3.42 |
| 19 | 21.3180 | 1302.1500 | 4.16805 | 2.95 |
| 20 | 21.5603 | 934.0500 | 4.12176 | 2.12 |
| 21 | 22.7144 | 2895.2700 | 3.91488 | 6.56 |
| 22 | 23.0344 | 873.2700 | 3.86120 | 1.98 |
| 23 | 23.6499 | 896.3900 | 3.76210 | 2.03 |
| 24 | 23.8846 | 677.3600 | 3.72566 | 1.54 |
| 25 | 24.1135 | 541.9600 | 3.69081 | 1.23 |
| 26 | 24.5829 | 1101.5100 | 3.62139 | 2.50 |
| 27 | 25.6984 | 747.6500 | 3.46667 | 1.69 |
| 28 | 27.4847 | 409.9700 | 3.24529 | 0.93 |
| 29 | 28.6738 | 595.5500 | 3.11335 | 1.35 |
| 30 | 29.6558 | 458.2200 | 3.01246 | 1.04 |
| 31 | 30.5073 | 307.7000 | 2.93029 | 0.70 |
| 32 | 31.4543 | 297.0900 | 2.84419 | 0.67 |
| 33 | 32.5040 | 149.3900 | 2.75470 | 0.34 |
| 34 | 33.6093 | 313.4700 | 2.66659 | 0.71 |
| 35 | 34.7208 | 244.1200 | 2.58373 | 0.55 |

TABLE 15-continued

Analytical data of the XRPD pattern of the crystal of the compound of formula (II)

| No. | Angle of 2θ (°) | Intensity (count) | d-Spacing (Å) | Relative intensity (%) |
|---|---|---|---|---|
| 36 | 35.2312 | 69.4200 | 2.54747 | 0.16 |
| 37 | 36.1110 | 234.9700 | 2.48739 | 0.53 |
| 38 | 38.2714 | 116.8700 | 2.35181 | 0.26 |
| 39 | 38.6975 | 227.9900 | 2.32688 | 0.52 |
| 40 | 39.3625 | 278.8000 | 2.28909 | 0.63 |
| 41 | 40.0020 | 522.8800 | 2.25396 | 1.18 |
| 42 | 41.6525 | 45.3600 | 2.16838 | 0.10 |
| 43 | 45.1338 | 174.7800 | 2.00889 | 0.40 |
| 44 | 46.5241 | 60.1500 | 1.95205 | 0.14 |
| 45 | 47.8708 | 55.1900 | 1.90023 | 0.13 |
| 46 | 49.5458 | 74.7000 | 1.83985 | 0.17 |
| 47 | 51.4415 | 65.5600 | 1.77641 | 0.15 |
| 48 | 55.6862 | 59.5900 | 1.64928 | 0.14 |

The present disclosure also provides a preparation method for the crystal of the compound of formula (II), comprising adding the compound of formula (I) into a mixed solvent of an alcohol solvent and water, and then slowly volatilizing at room temperature for 10 days, and precipitating a solid to obtain the crystal of the compound of formula (II).

Taking about 5 mg of the compound of formula (I), putting into a 2 mL brown sample bottle, adding 500 μL of methanol: water (4:1) until fully dissolve, and then standing at room temperature for 10 days to obtain the crystal of the compound of formula (II).

The present disclosure also provides the crystal of the compound of formula (II), which is characterized in that the X-ray powder diffraction pattern thereof comprises characteristic diffraction peaks at the following angles of 2θ: 9.56±0.30°, 19.29±0.30° and 19.78±0.20°, wherein n is preferably 2.

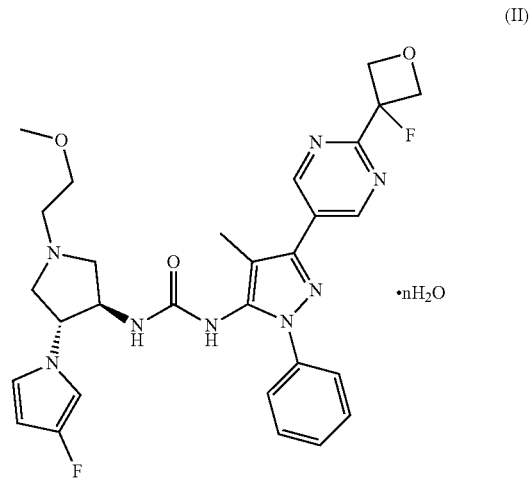 [SMILES: COCCN1C[C@@H](n2ccc(F)c2)[C@H](NC(=O)Nc2c(C)c(-c3cnc(C4(F)COC4)nc3)nn2-c2ccccc2)C1]

(II)

In some embodiments of the present disclosure, the X-ray powder diffraction pattern of the crystal of the compound of formula (II) comprises characteristic diffraction peaks at the following angles of 2θ: 9.56±0.30°, 12.08±0.30°, 19.29±0.30° and 19.78±0.20°.

In some embodiments of the present disclosure, the X-ray powder diffraction pattern of the crystal of the compound of formula (II) comprises characteristic diffraction peaks at the following angles of 2θ: 9.56±0.30°, 10.75±0.30°, 12.08±0.30°, 19.29±0.30°, 19.78±0.20° and 22.82±0.30°.

In some embodiments of the present disclosure, the X-ray powder diffraction pattern of the crystal of the compound of formula (II) comprises characteristic diffraction peaks at the following angles of 2θ: 4.91°, 9.56°, 10.75°, 12.08°, 13.70°, 14.78°, 15.60°, 17.62°, 19.29°, 19.78°, 20.55°, 21.58°, 22.82°, 23.85°, 24.29°, 24.74°, 25.86°, 26.59°, 27.70°, 28.56°, 28.94°, 30.67°, 31.50° and 37.80°.

In some embodiments of the present disclosure, the X-ray powder diffraction pattern of the crystal of the compound of formula (II) comprises characteristic diffraction peaks at the following angles of 2θ: 9.0233°, 9.3138°, 9.4821°, 10.5145°, 10.7290°, 11.9125°, 14.5999°, 18.9000°, 19.0764°, 19.2297°, 19.5885°, 19.7576°, 20.2743°, 20.4715°, 21.3180°, 21.5603°, 22.7144°, 23.6499° and 24.5829°.

In some embodiments of the present disclosure, the crystal of the compound of formula (II) is selected from the crystal form E and the crystal of the compound of formula (II).

The present disclosure also provides a preparation method for the crystal of the compound of formula (II), comprising adding the compound of formula (I) into an alcohol solvent, a nitrile solvent, an ester solvent or a mixed solvent of alcohol, nitrile and water, stirring at a certain temperature for a certain time, then centrifuging, and drying a residue to obtain a crystal form of the compound of formula (II).

In some embodiments of the present disclosure, the alcohol solvent is selected from methanol and ethanol, the nitrile solvent is selected from acetonitrile, and the ester solvent is selected from ethyl acetate.

In some embodiments of the present disclosure, the mixed solvent of alcohol, nitrile and water is selected from methanol and water, ethanol and water, and acetonitrile and water.

In some embodiments of the present disclosure, a temperature for the stirring is selected from 20° C. to 60° C.

In some embodiments of the present disclosure, a time for the stirring is selected from 48 hours to 96 hours.

The present disclosure also provides use of the above crystal form A or B or C or D or E or F or the crystal form E prepared according to the above method in the manufacture of medicaments for treating diseases associated with pain, cancer, inflammation, neurodegenerative diseases, and certain infectious diseases.

Technical Effect

Each crystal form of the compounds of the present disclosure is stable, less affected by light, heat and humidity, and has good administration efficacy in vivo, and a promising pharmaceutical prospect; the compound of formula (I) has significant TrkA enzyme inhibitory effect, high unbound rate of plasma protein, low risk of drug-drug interaction and good metabolic stability of liver microsomes; the crystal form E of the compound of formula (I) has good pharmacokinetic properties and bioavailability.

Definition and Description

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions of the embodiments of the present disclosure are carried out in a suitable solvent, and the solvent should be suitable for the chemical change of the present disclosure, and the reagents and materials required. In order to obtain the compounds of the present disclosure, it is sometimes necessary for those skilled in the art to modify or select the synthetic steps or reaction schemes based on the existing embodiments.

The structures of the compounds of the present disclosure can be confirmed by conventional methods well known to those skilled in the art. If the present disclosure relates to an absolute configuration of the compound, the absolute configuration can be confirmed by conventional technical means in the art. For example, in single crystal X-ray diffraction (SXRD), diffraction intensity data of a cultured single crystal are collected by a Bruker D8 venture diffractometer, using CuKα radiation as a light source and φ/ω scanning as a scanning mode. After collecting relevant data, the absolute configuration can be confirmed by further analyzing the structure of the crystal form with a direct method (Shelxs97).

The present disclosure will be specifically described below by way of embodiments, but the scope of the present disclosure is not limited thereto.

All solvents used in the present disclosure are commercially available and can be directly used without further purification.

The solvents used in the present disclosure are commercially available. The present disclosure employs the following abbreviations: EtOH represents ethanol; MeOH represents methanol; TFA represents trifluoroacetic acid; TsOH represents p-toluenesulfonic acid; mp represents melting point; $EtSO_3H$ represents ethanesulfonic acid; $MeSO_3H$ represents methanesulfonic acid; THF represents tetrahydrofuran; and EtOAc represents ethyl acetate.

Compounds are named according to conventional naming principles in the field or by ChemDraw® software, and the commercially available compounds use their vendor directory names.

X-Ray Powder Diffractometer (XRPD) Method in the Present Disclosure

Instrument model: X'Pert3 X-ray diffractometer from PANalytical

Detection method: about 10 mg of the sample was used for XRPD detection.

Detailed XRPD parameters are as follows:
Radiation source: Cu, kα (Kα1=1.540598 Å, Kα2=1.544426 Å, intensity ratio of Kα2/Kα1: 0.5)
X-ray tube voltage: 45 kV, X-ray tube current: 40 mA
Divergent slit: fixed ⅛ deg
First soller slit: 0.04 rad, second soller slit: 0.04 rad
Receiving slit: none, anti-scattering slit: 7.5 mm.
Measurement time: 5 min
Scanning angle range: 3-40 deg
Step width angle: 0.0263 deg
Step time: 46.665 seconds
Rotation speed of sample tray: 15 rpm X-ray Powder Diffractometer (XRPD) Method in the Present Disclosure Diffractometer system: PNalytical XPERT-PRO
Detailed XRPD parameters are as follows:
Radiation source: Cu, kα (Kα1=1.54060 Å, Kα2=1.54443 Å, Kβ=1.39225 Å, intensity ratio of Kα2/Kα1: 0.5)
X-ray tube voltage: 40 kV, X-ray tube current: 40 mA Divergent slit: fixed 0.2177 deg
Scanning type: continuous
Scanning angle range: 3.0131-59.9791 deg
Step width angle: 0.0263 deg
Step time: 0.0260
Scanning step time: 14.0927 seconds Differential Scanning Calorimeter (DSC) Method in the Present Disclosure Instrument model: TA Q2000/Discovery 2500 differential scanning calorimeter Detection method: A sample (about 1-5 mg) was placed in a DSC aluminum tray for detection, and the sample was heated from 25° C. (room temperature) to before the decomposition of the sample at a heating rate of 10° C./min under the condition of 50 mL/min nitrogen.

Thermal Gravimetric Analyzer (TGA) Method in the Present Disclosure

Instrument model: TA Q5000/Discovery 5500 thermogravimetric analyzer

Detection method: A sample (about 1-5 mg) was placed in the TGA aluminum tray for detection, and the sample was heated from room temperature to 350° C. at a heating rate of 10° C./min under the condition of 10 mL/min nitrogen.

Dynamic Vapor Sorption (DVS) Method in the Present Disclosure

Instrument model: Intrinsic dynamic vapor sorption instrument

Detection conditions: A sample (10-30 mg) was placed in a DVS sample tray for detection.

Detailed DVS parameters are as follows:
Temperature: 25° C.
Balance: dm/dt=0.002%/min (shortest: 10 min, longest: 180 min)
RH (%) test step: 10 (0-90%), 5 (90-95%)
RH (%) test step range: 70-95-0-95

The evaluation classification of hygroscopicity is as follows:

| Classification of hygroscopicity | ΔW % |
| --- | --- |
| Deliquescence | Absorbing sufficient water to form liquid |
| Highly hygroscopic | ΔW % ≥ 15% |
| hygroscopic | 15% > ΔW % ≥ 2% |
| Slightly hygroscopic | 2% > ΔW % ≥ 0.2% |
| non-hygroscopic or almost non-hygroscopic | ΔW % < 0.2% |

Note:
ΔW % indicates the hygroscopic weight gain of the test compound at 25 ± 1° C. and 80 ± 2% RH.

High Performance Liquid Chromatograph (HPLC) Method in the Present Disclosure

Detailed parameters are as follows:

| | |
| --- | --- |
| Chromatographic column model | YMC-Pack ODS-A (250 mm*4.6 mm, 5 μm) or equivalent |
| Flow rate: | 1.0 mL/min |
| Detection wavelength: | 220 nm |
| Injection tray temperature: | Room temperature |
| Column temperature: | 35° C. |
| Injection volume: | 10 μL |
| Running time: | 68 min |
| Mobile phase: | Mobile phase A: 25 mM disodium hydrogen phosphate buffer (the pH was adjusted to 3.0 with phosphoric acid) Mobile phase B: acetonitrile |

| | Time (min) | Mobile phase A (%) | Mobile phase B (%) |
| --- | --- | --- | --- |
| Gradient: | 0 | 90 | 10 |
| | 15 | 90 | 10 |
| | 35 | 60 | 40 |
| | 52 | 25 | 75 |
| | 57 | 25 | 75 |
| | 60 | 90 | 10 |
| | 68 | 90 | 10 |

DETAILED DESCRIPTION OF THE PREFERRED EMBODIMENT

Figure 1:
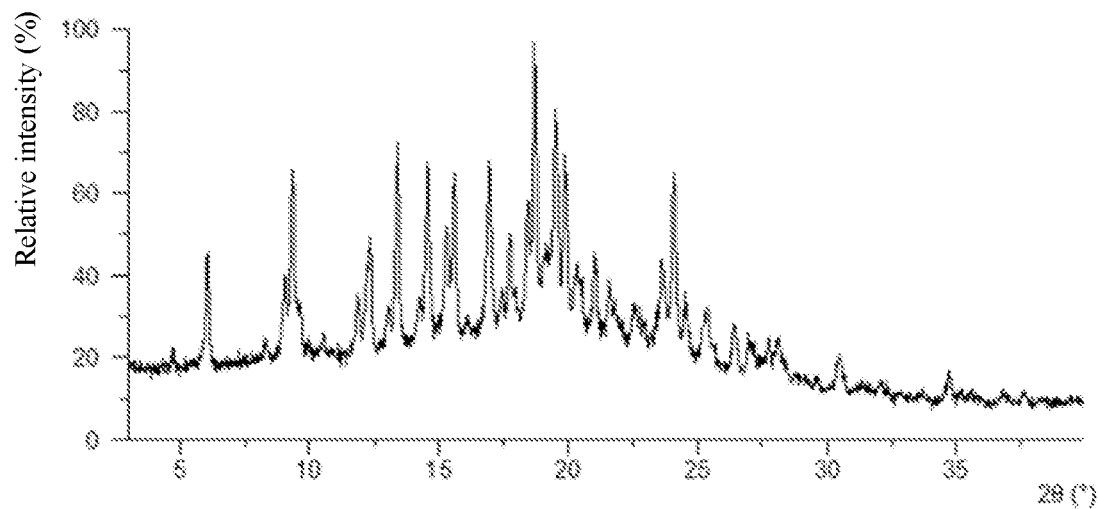
FIG. 1 is the XRPD pattern of the crystal form A of the compound of formula (I) measured by Cu-Kα radiation.
Figure 2:
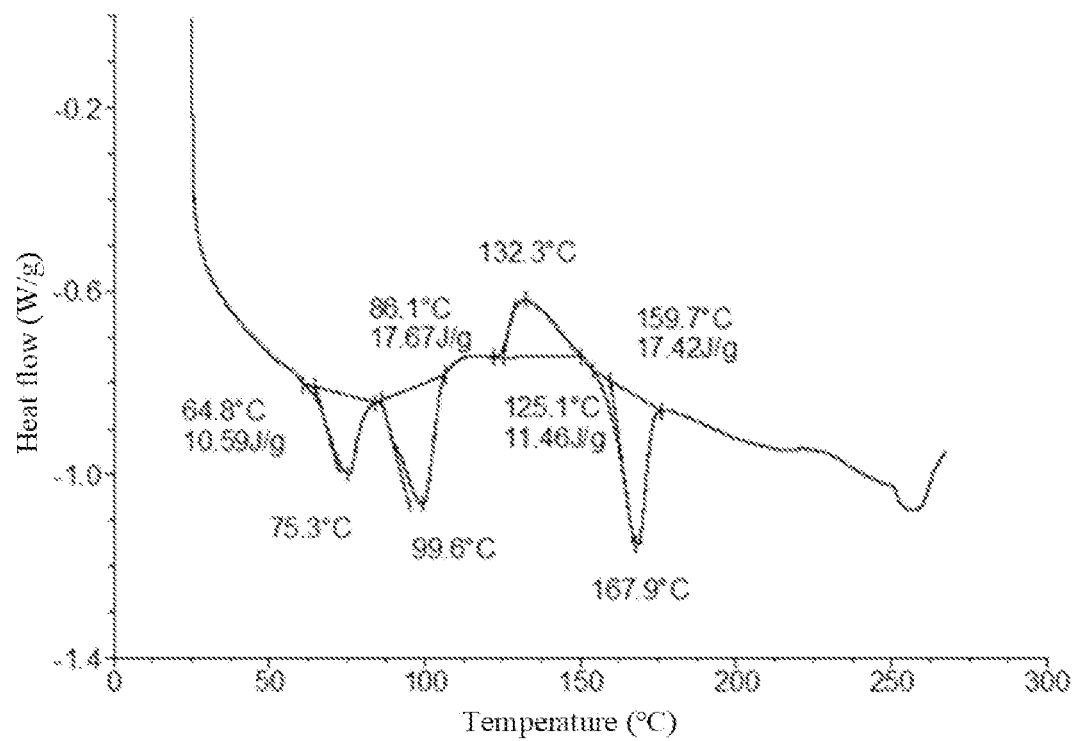
FIG. 2 is the DSC pattern of the crystal form A of the compound of formula (I).
Figure 3:
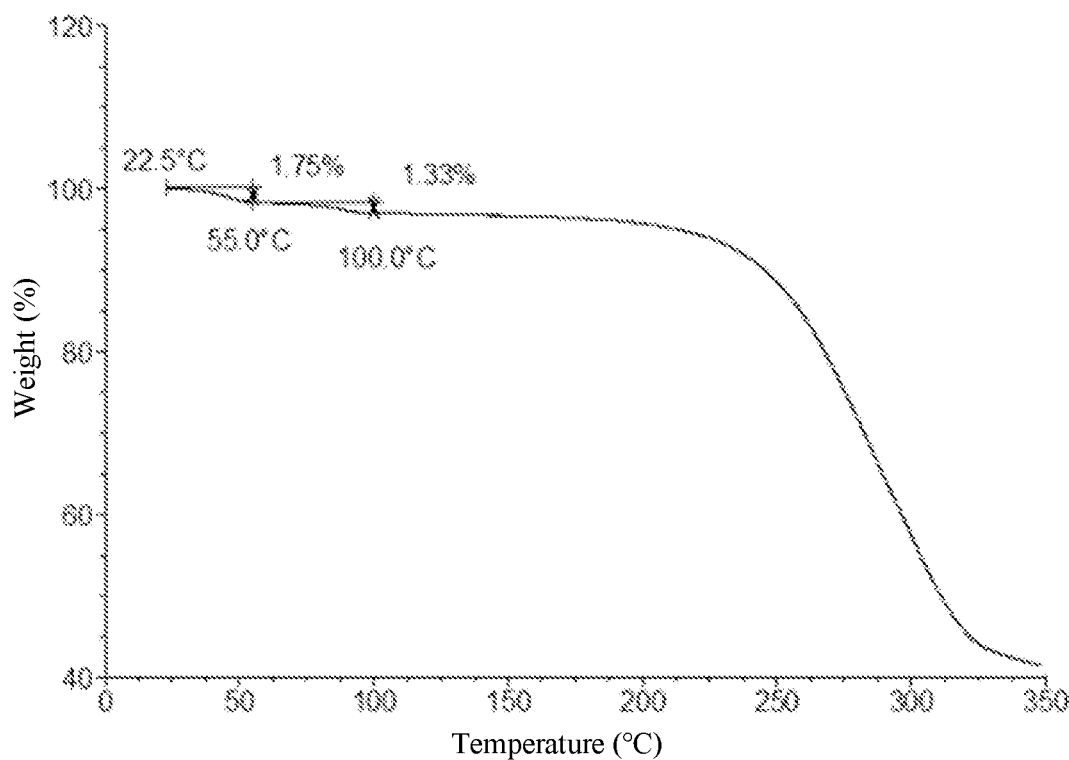
FIG. 3 is the TGA pattern of the crystal form A of the compound of formula (I).
Figure 4:
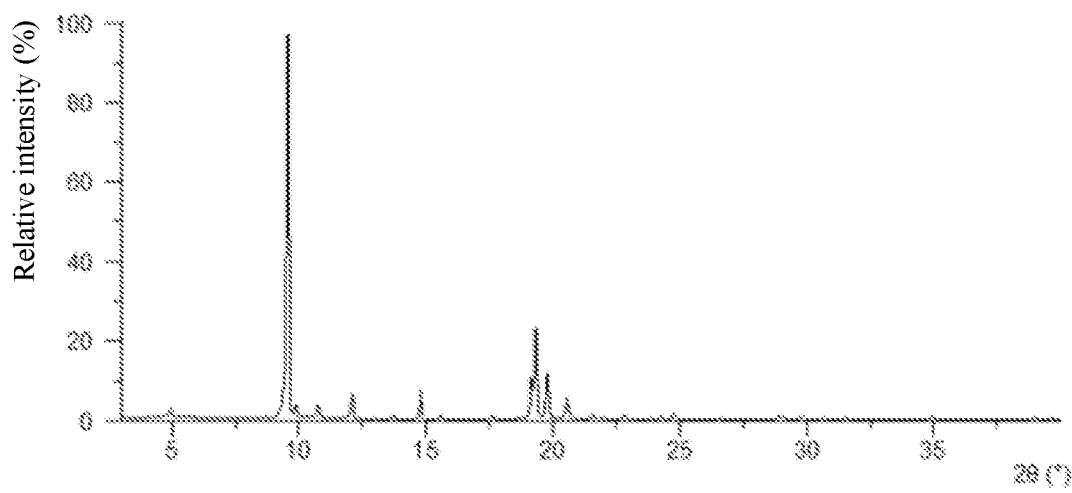
FIG. 4 is the XRPD pattern of the crystal form B of the compound of formula (I) measured by Cu-Kα radiation.
Figure 5:
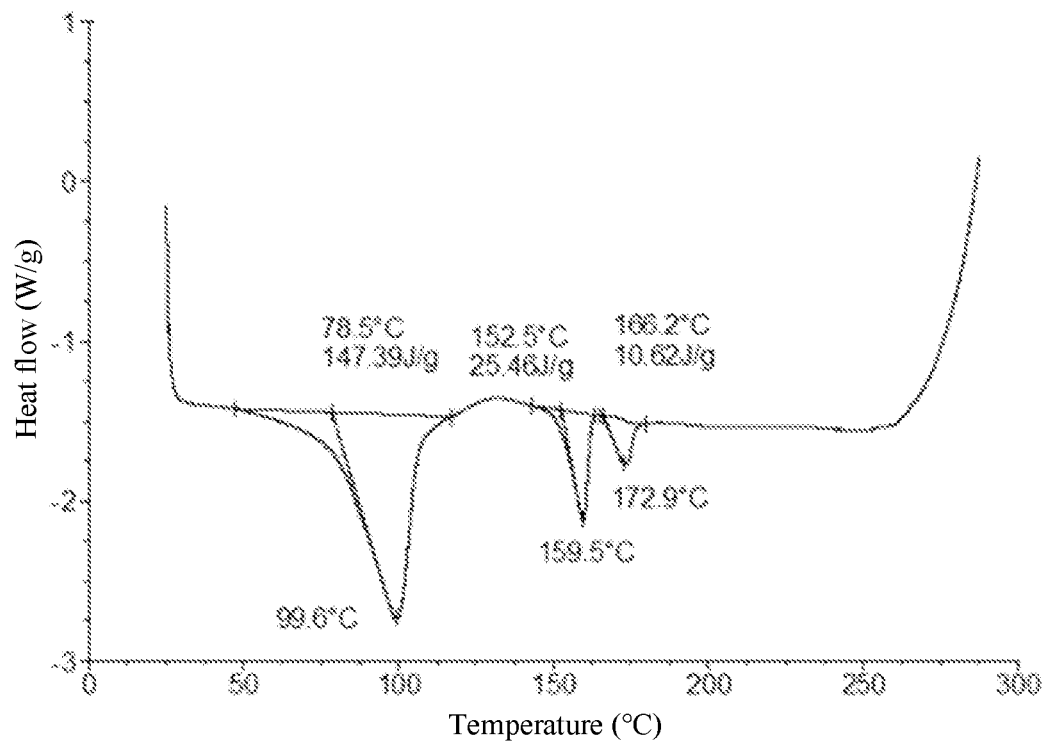
FIG. 5 is the DSC pattern of the crystal form B of the compound of formula (I).
Figure 6:
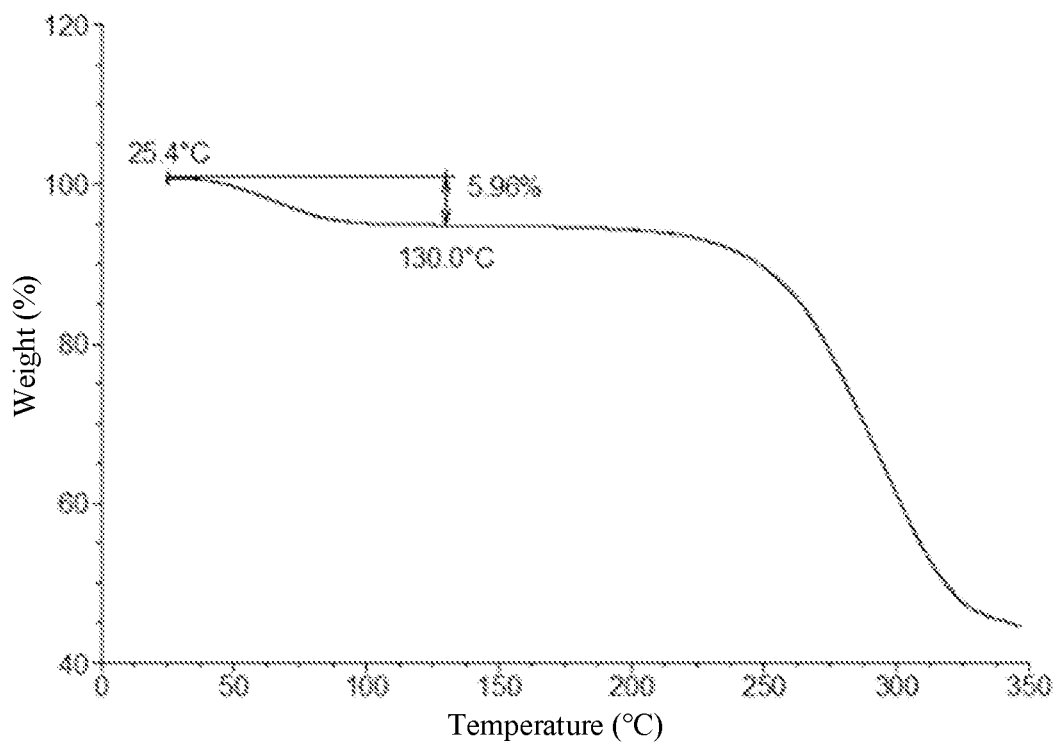
FIG. 6 is the TGA pattern of the crystal form B of the compound of formula (I).
Figure 7:
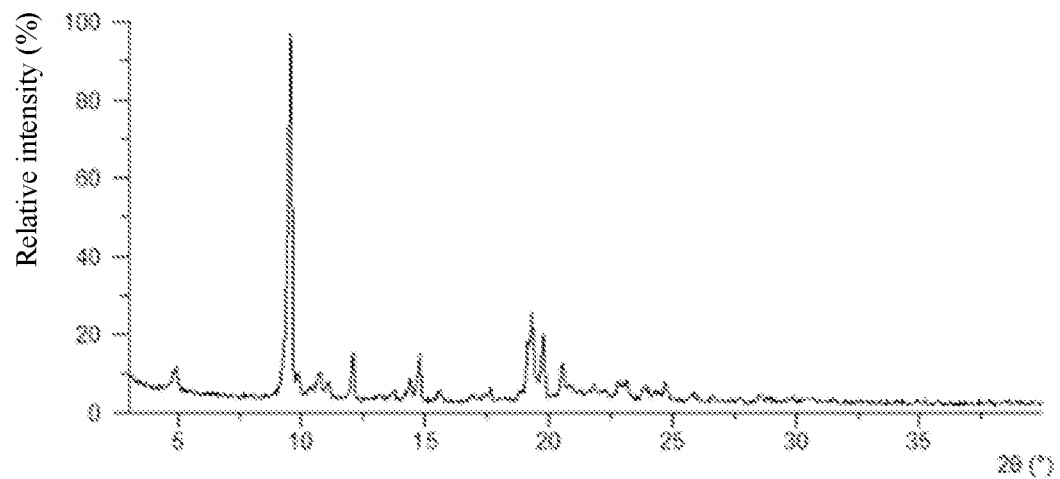
FIG. 7 is the XRPD pattern of the crystal form C of the compound of formula (I) measured by Cu-Kα radiation.
Figure 8:
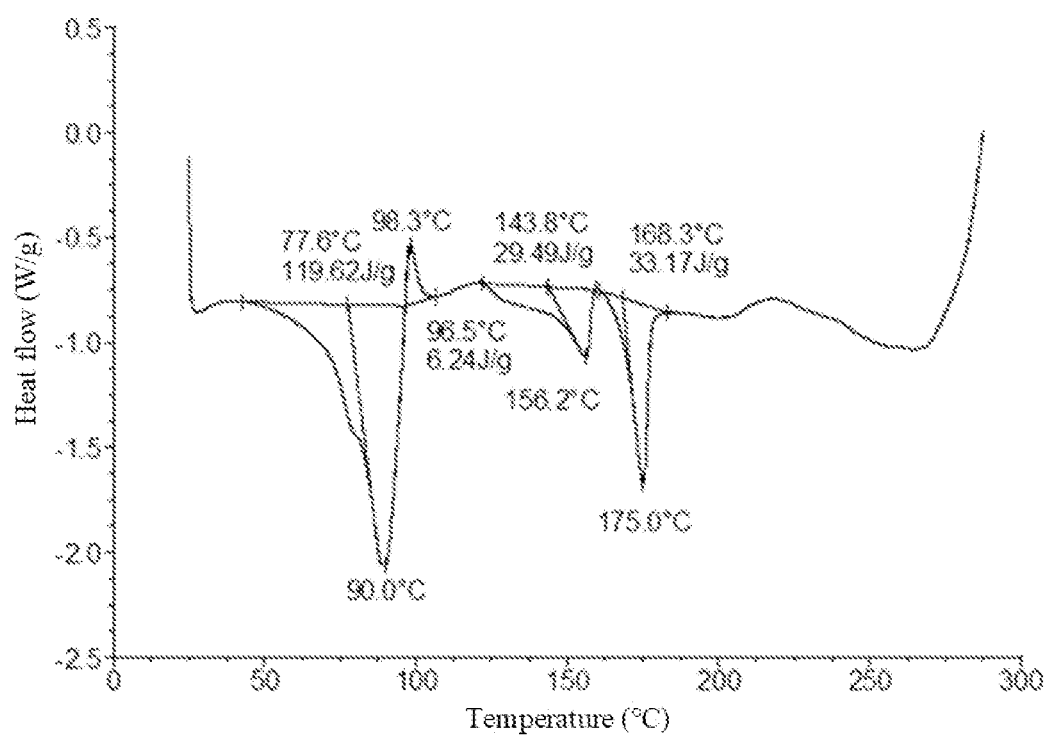
FIG. 8 is the DSC pattern of the crystal form C of the compound of formula (I).
Figure 9:
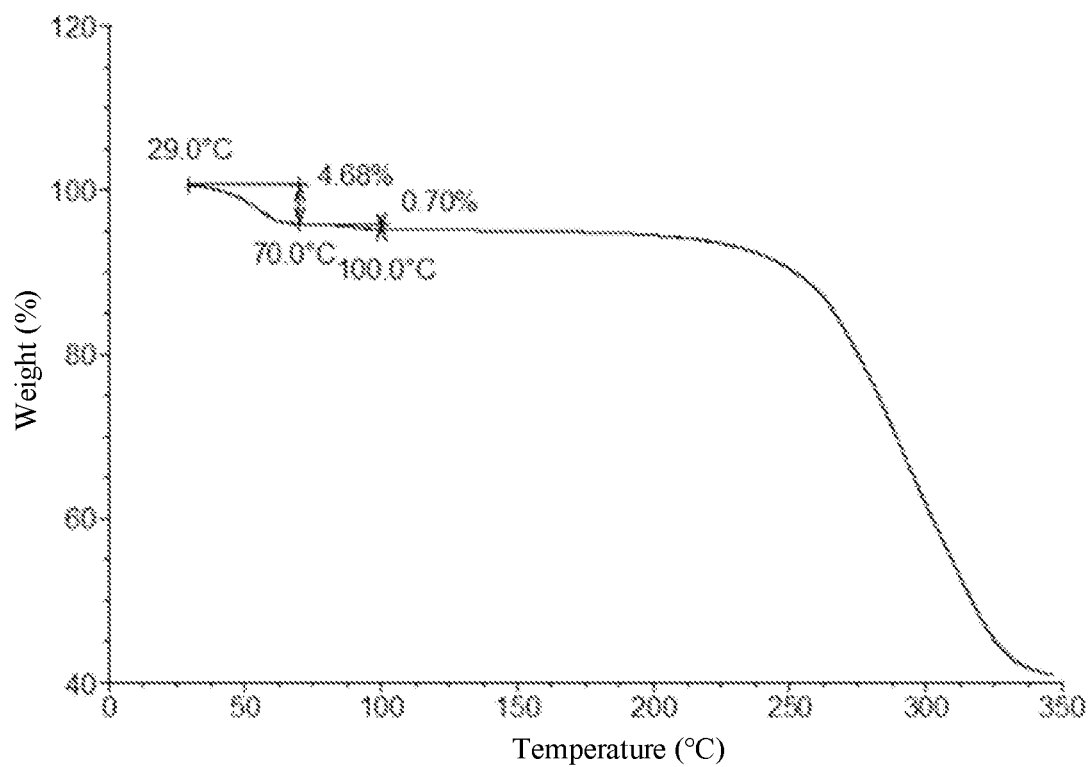
FIG. 9 is the TGA pattern of the crystal form C of the compound of formula (I).
Figure 10:
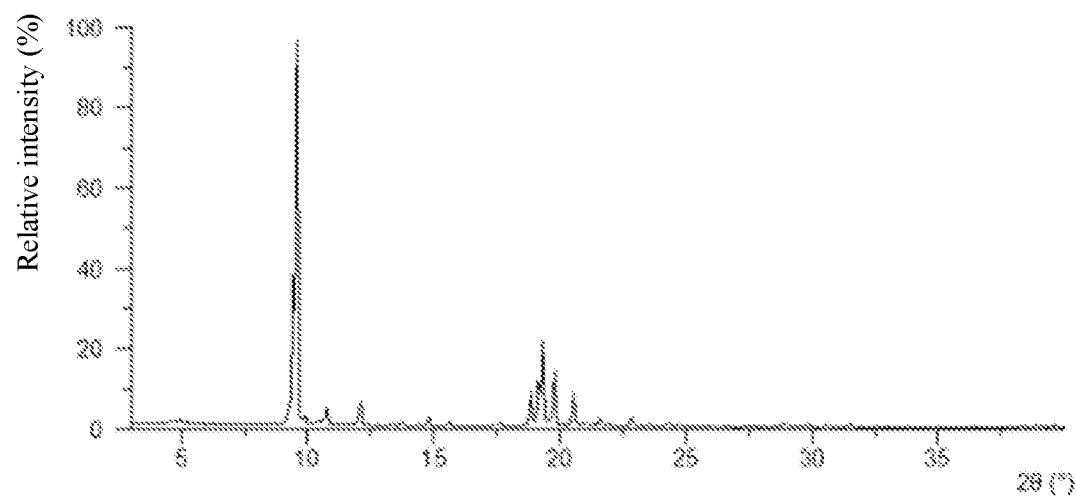
FIG. 10 is the XRPD pattern of the crystal form D of the compound of formula (I) measured by Cu-Kα radiation.
Figure 11:
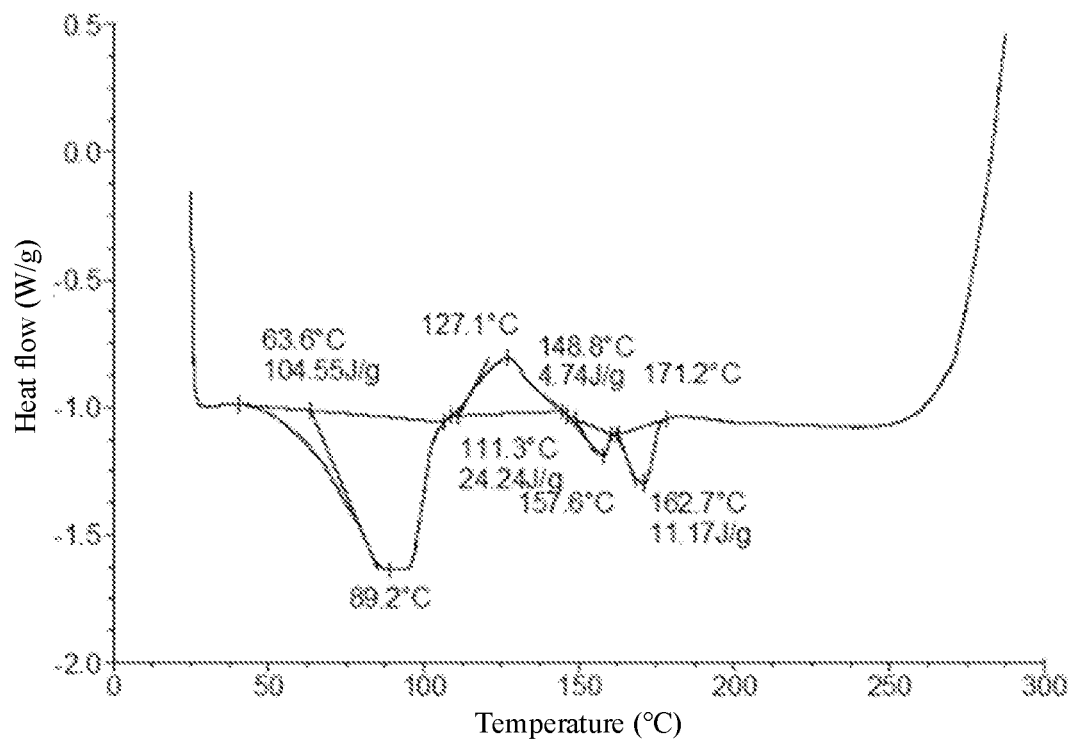
FIG. 11 is the DSC pattern of the crystal form D of the compound of formula (I).
Figure 12:
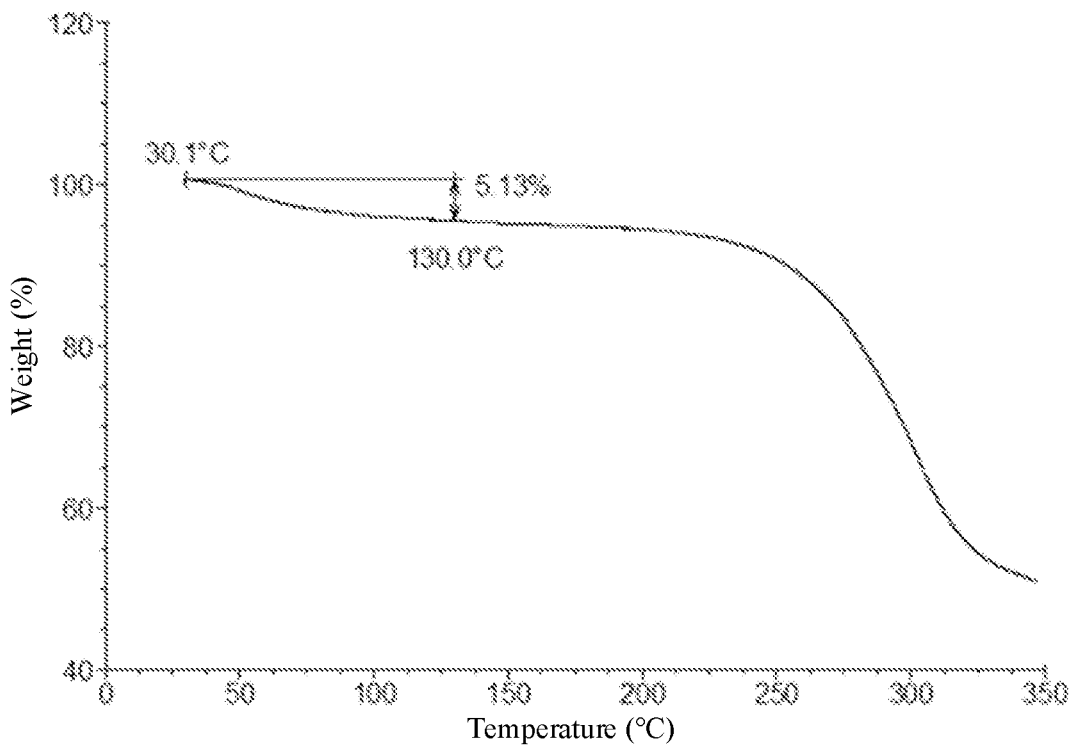
FIG. 12 is the TGA pattern of the crystal form D of the compound of formula (I).

In order to better understand the contents of the present disclosure, the following embodiments further illustrate the present disclosure, but the present disclosure is not limited thereto.

Embodiment 1: Preparation of the Compound of Formula (I)
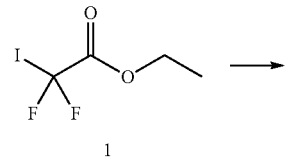
1
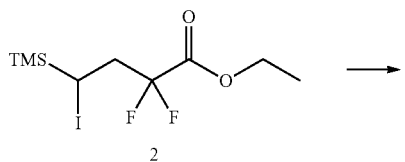
2
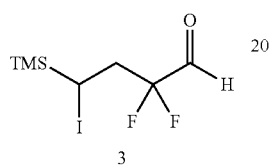
3
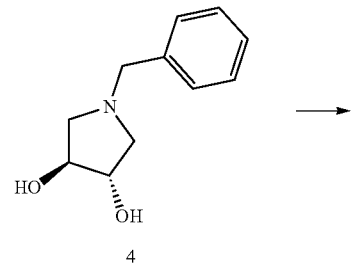
4
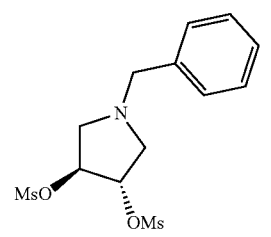
5
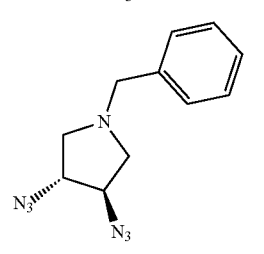
6
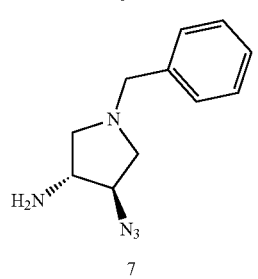
7
-continued
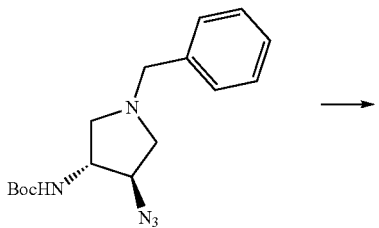
8
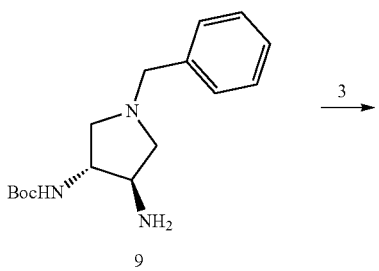
9
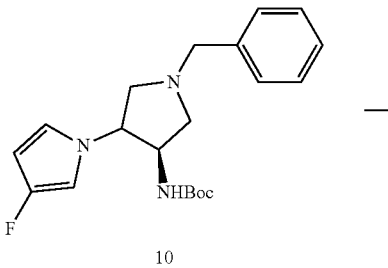
10
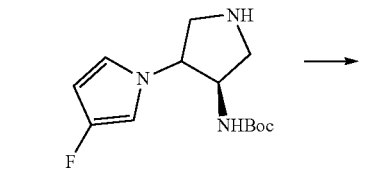
11
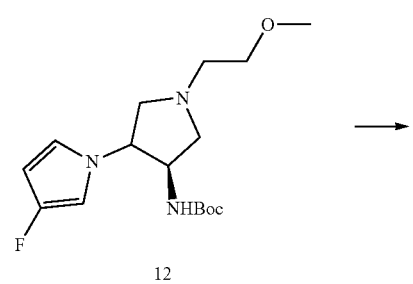
12
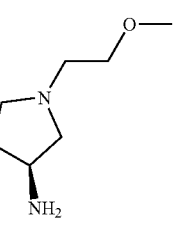
13

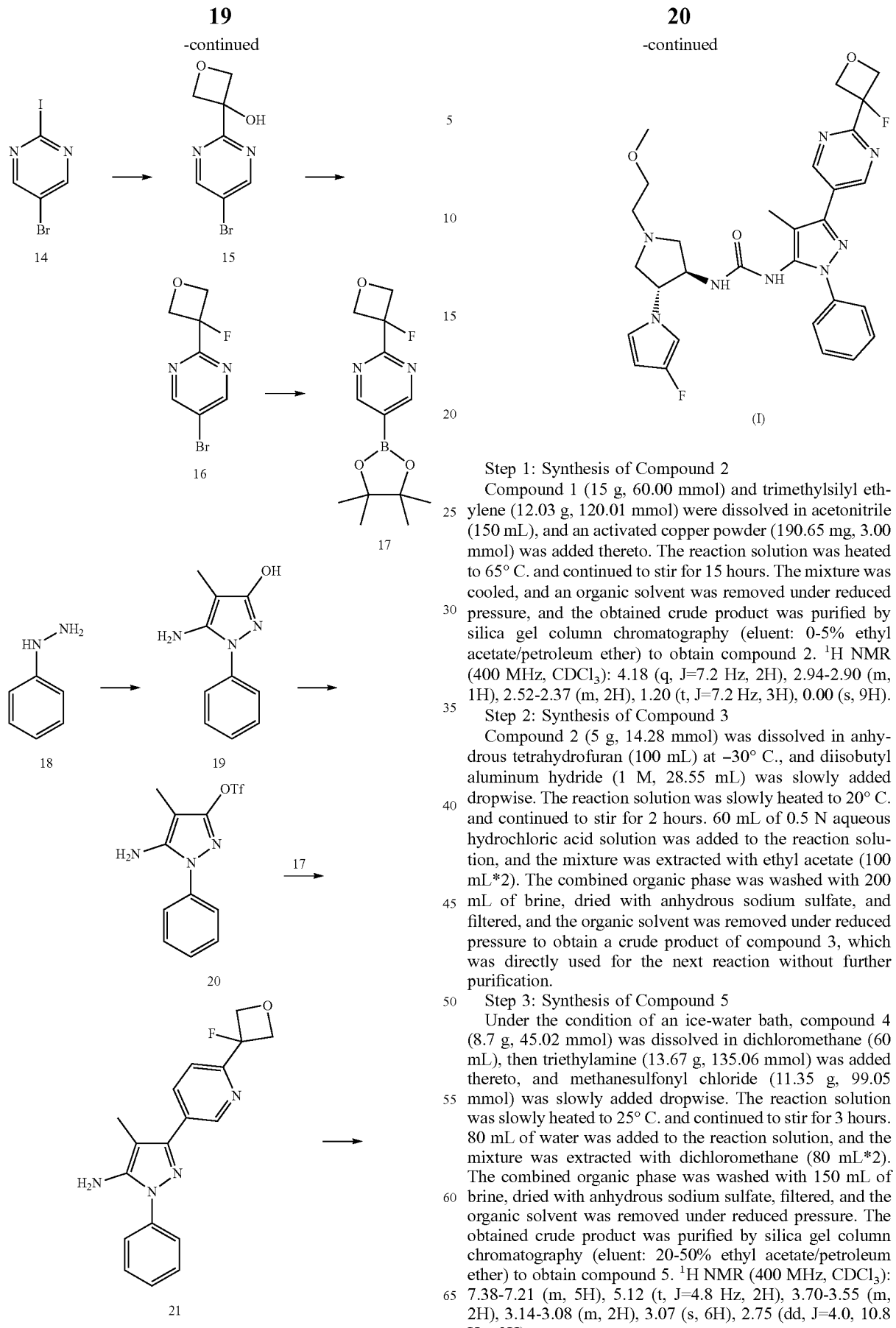

Step 1: Synthesis of Compound 2

Compound 1 (15 g, 60.00 mmol) and trimethylsilyl ethylene (12.03 g, 120.01 mmol) were dissolved in acetonitrile (150 mL), and an activated copper powder (190.65 mg, 3.00 mmol) was added thereto. The reaction solution was heated to 65° C. and continued to stir for 15 hours. The mixture was cooled, and an organic solvent was removed under reduced pressure, and the obtained crude product was purified by silica gel column chromatography (eluent: 0-5% ethyl acetate/petroleum ether) to obtain compound 2. $^1$H NMR (400 MHz, CDCl$_3$): 4.18 (q, J=7.2 Hz, 2H), 2.94-2.90 (m, 1H), 2.52-2.37 (m, 2H), 1.20 (t, J=7.2 Hz, 3H), 0.00 (s, 9H).

Step 2: Synthesis of Compound 3

Compound 2 (5 g, 14.28 mmol) was dissolved in anhydrous tetrahydrofuran (100 mL) at −30° C., and diisobutyl aluminum hydride (1 M, 28.55 mL) was slowly added dropwise. The reaction solution was slowly heated to 20° C. and continued to stir for 2 hours. 60 mL of 0.5 N aqueous hydrochloric acid solution was added to the reaction solution, and the mixture was extracted with ethyl acetate (100 mL*2). The combined organic phase was washed with 200 mL of brine, dried with anhydrous sodium sulfate, and filtered, and the organic solvent was removed under reduced pressure to obtain a crude product of compound 3, which was directly used for the next reaction without further purification.

Step 3: Synthesis of Compound 5

Under the condition of an ice-water bath, compound 4 (8.7 g, 45.02 mmol) was dissolved in dichloromethane (60 mL), then triethylamine (13.67 g, 135.06 mmol) was added thereto, and methanesulfonyl chloride (11.35 g, 99.05 mmol) was slowly added dropwise. The reaction solution was slowly heated to 25° C. and continued to stir for 3 hours. 80 mL of water was added to the reaction solution, and the mixture was extracted with dichloromethane (80 mL*2). The combined organic phase was washed with 150 mL of brine, dried with anhydrous sodium sulfate, filtered, and the organic solvent was removed under reduced pressure. The obtained crude product was purified by silica gel column chromatography (eluent: 20-50% ethyl acetate/petroleum ether) to obtain compound 5. $^1$H NMR (400 MHz, CDCl$_3$): 7.38-7.21 (m, 5H), 5.12 (t, J=4.8 Hz, 2H), 3.70-3.55 (m, 2H), 3.14-3.08 (m, 2H), 3.07 (s, 6H), 2.75 (dd, J=4.0, 10.8 Hz, 2H).

Step 4: Synthesis of Compound 6

Compound 5 (15 g, 42.93 mmol) was dissolved in N,N-dimethylformamide (100 mL), and sodium azide (8.37 g, 128.78 mmol) was added thereto. The reaction solution was heated to 100° C. and continued to stir for 16 hours. The mixture was cooled, and 200 mL of water was added to the reaction solution and the mixture was extracted with ethyl acetate (200 mL*3). The combined organic phase was washed with water (300 mL*2) and brine (300 mL) in turn, dried with anhydrous sodium sulfate, filtered, and the organic solvent was removed under reduced pressure. The obtained crude product was purified by silica gel column chromatography (eluent: 0-2% ethyl acetate/petroleum ether) to obtain compound 6. $^1$H NMR (400 MHz, CDCl$_3$): 7.43-7.28 (m, 5H), 3.90 (t, J=4.4 Hz, 2H), 3.75-3.61 (m, 2H), 3.02 (dd, J=6.4, 10.0 Hz, 2H), 2.70-2.58 (m, 2H), Step 5: Synthesis of Compound 7

Compound 6 (7 g, 28.77 mmol) was dissolved in tetrahydrofuran (60 mL), then water (1.04 g, 57.55 mmol) was added thereto, and triphenylphosphine (6.79 g, 25.90 mmol) was slowly added in batches. The reaction solution was stirred at 25° C. until no gas was released, heated to 80° C. and continued to stir for 1 hour. The mixture was cooled, and the organic solvent was removed under reduced pressure. 80 mL of 4 N aqueous hydrochloric acid solution was added to the obtained crude product, and the mixture was extracted with 80 mL of dichloromethane. The pH of the aqueous phase was adjusted to about 10 with ammonia water, and extracted with dichloromethane (80 mL*2). The combined organic phase was washed with 100 mL of brine, dried with anhydrous sodium sulfate, and filtered, and the organic solvent was removed under reduced pressure to obtain a crude product of compound 7, which was directly used for the next reaction without further purification. $^1$H NMR (400 MHz, CDCl$_3$): 7.35-7.24 (m, 5H), 3.64 (q, J=13.2 Hz, 2H), 3.56 (td, J=3.6, 6.8 Hz, 1H), 3.48-3.40 (m, 1H), 3.07-2.90 (m, 2H), 2.64 (dd, J=4.4, 10.4 Hz, 1H), 2.31 (dd, J=5.2, 9.6 Hz, 1H).

Step 6: Synthesis of Compound 8

Compound 7 (6.4 g, 29.46 mmol) was dissolved in dichloromethane (60 mL), and triethylamine (5.96 g, 58.91 mmol) and di-tert-butyl dicarbonate (7.71 g, 35.35 mmol) were added thereto. The reaction solution was continued to stir at 25° C. for 15 hours. The organic solvent was removed under reduced pressure, and the obtained crude product was purified by silica gel column chromatography (eluent: 0-10% ethyl acetate/petroleum ether) to obtain compound 8. $^1$H NMR (400 MHz, CDCl$_3$): 7.40-7.25 (m, 5H), 4.87 (s, 1H), 4.07 (s, 1H), 3.81 (s, 1H), 3.70-3.56 (m, 2H), 3.07 (dd, J=6.8, 10.4 Hz, 1H), 2.93-2.77 (m, 1H), 2.56-2.32 (m, 2H), 1.47 (s, 9H).

Step 7: Synthesis of Compound 9

Compound 8 (8.8 g, 27.73 mmol) was dissolved in methanol (100 mL), and palladium carbon (0.5 g, 27.73 mmol, 10% purity) was added thereto. The reaction solution was continued to stir at 20° C. for 3 hours under a hydrogen pressure of 15 psi. The reaction solution was filtered through diatomite, and the organic solvent was removed under reduced pressure to obtain a crude product of compound 9, which was be directly used for the next reaction without further purification. $^1$H NMR (400 MHz, CDCl$_3$): 7.33-7.25 (m, 5H), 5.04 (d, J=6.4 Hz, 1H), 3.70 (s, 1H), 3.63-3.54 (m, 2H), 3.34-3.23 (m, 1H), 3.07 (t, J=8.4 Hz, 1H), 2.82 (dd, J=7.2, 9.6 Hz, 1H), 2.51-2.43 (m, 1H), 2.21-2.09 (m, 1H), 1.44 (s, 9H).

Step 8: Synthesis of Compound 10

Compound 9 (2.35 g, 8.06 mmol) was dissolved in acetonitrile (50 mL), and compound 3 (1.98 g, 6.45 mmol) was added thereto. The reaction solution was heated to 50° C. and continued to stir for 15 hours. The mixture was cooled, and the organic solvent was removed under reduced pressure. The obtained crude product was purified by silica gel column chromatography (eluent: 0-30% ethyl acetate/petroleum ether) to obtain compound 10. $^1$H NMR (400 MHz, CDCl$_3$): 7.40-7.27 (m, 5H), 6.61 (s, 1H), 6.53 (s, 1H), 5.87 (dd, J=2.0, 2.8 Hz, 1H), 4.82 (s, 1H), 4.29-4.17 (m, 1H), 4.15-4.05 (m, 1H), 3.73-3.58 (m, 2H), 3.16-3.03 (m, 2H), 2.85-2.76 (m, 1H), 2.58-2.43 (m, 1H), 1.43 (s, 9H).

Step 9: Synthesis of Compound 11

Compound 10 (840 mg, 2.34 mmol) was dissolved in toluene (30 mL), and diisopropylethylamine (422.86 mg, 3.27 mmol) was added thereto. Under the condition of an ice-water bath, 1-chloroethyl chloroformate (434.35 mg, 3.04 mmol) was slowly added dropwise. The reaction solution was heated to 90° C. and continued to stir for 1 hour. The reaction solution was cooled, and the organic solvent was removed under reduced pressure. Methanol (30 mL) was added thereto, and the mixture was stirred at 20° C. for 17 hours. The organic solvent was removed under reduced pressure to obtain a crude product of compound 11, which was directly used in the next reaction without further purification. MS m/z: 270.1 [M+1]$^+$.

Step 10: Synthesis of Compound 12

Compound 11 (630 mg, 2.34 mmol) was dissolved in N,N-dimethylformamide (10 mL), and diisopropylethylamine (906.98 mg, 7.02 mmol) and 2-bromoethyl methyl ether (536.92 mg, 3.51 mmol) were added thereto. The reaction solution was continued to stir at 20° C. for 64 hours. The reaction solution was diluted with 100 mL of ethyl acetate, washed with 60 mL of water and 60 mL of brine in turn, dried with anhydrous sodium sulfate, and filtered. The organic solvent was removed under reduced pressure. The obtained crude product was purified by silica gel column chromatography (eluent: 25%-60% ethyl acetate/petroleum ether) to obtain compound 12. $^1$H NMR (400 MHz, CDCl$_3$): 6.60 (s, 1H), 6.54 (s, 1H), 5.88 (dd, J=2.0, 2.8 Hz, 1H), 4.91 (s, 1H), 4.24 (s, 1H), 4.12-4.05 (m, 1H), 3.51 (t, J=5.6 Hz, 2H), 3.37 (s, 3H), 3.19 (s, 1H), 3.08 (d, J=8.0 Hz, 1H), 2.84-2.64 (m, 3H), 1.43 (s, 9H).

Step 11: Synthesis of Compound 13

Compound 12 (100 mg, 305.44 μmol) was dissolved in dichloromethane (2 mL), and trifluoroacetic acid (2 mL) was added thereto. The reaction solution was continued to stir at 20° C. for 0.5 hours. The organic solvent was removed under reduced pressure to obtain a crude product of compound 13, which was directly used in the next reaction without further purification. MS m/z: 228.1 [M+1]$^+$.

Step 12: Synthesis of Compound 15

Compound 14 (4.0 g, 14.04 mmol) was dissolved in anhydrous tetrahydrofuran (40 mL), cooled to −78° C. Oxetanone (1.2 g, 16.85 mmol) was added thereto, and n-butyl lithium (2.5 M, 8.4 mL) solution was slowly added thereto dropwise. The reaction solution was continued to stir at this temperature for 20 minutes. Saturated aqueous ammonium chloride solution (20 mL) was slowly added to the reaction solution, and the mixture was extracted with ethyl acetate (50 mL*3). The combined organic phases were washed with saturated sodium chloride solution (50 mL), dried with anhydrous sodium sulfate, filtered, and the organic solvent was removed under reduced pressure. The obtained crude product was purified by silica gel column chromatography (eluent: 0-20% ethyl acetate/petroleum ether) to obtain compound 15. $^1$H NMR: (400 MHz, CDCl$_3$): 8.89 (s, 2H), 5.06-4.95 (m, 4H).

Step 13: Synthesis of Compound 16

Compound 15 (1.8 g, 7.75 mmol) was dissolved in dichloromethane (13 mL) under an ice water bath, and a dichloromethane (4 mL) solution of diethylaminosulfur trifluoride (2.5 g, 15.50 mmol) was added thereto. The reaction solution was continued to stir at this temperature for 20 minutes. The reaction solution was added with water (20 mL), and extracted with ethyl acetate (50 mL*3). The combined organic phases were washed with saturated sodium chloride solution (50 mL), dried with anhydrous sodium sulfate, filtered, and the organic solvent was removed under reduced pressure. The obtained crude product was purified by silica gel column chromatography (eluent: 0-10% ethyl acetate/petroleum ether) to obtain compound 16. $^1$H NMR (400 MHz, CDCl$_3$): 8.91 (s, 2H), 5.20-5.05 (m, 4H).

Step 14: Synthesis of Compound 17

Compound 16 (300 mg, 1.29 mmol) was dissolved in 1,4-dioxane (8.0 mL), and then bis(pinacolato)diboron (392 mg, 1.54 mmol) and potassium acetate (379 mg, 3.86 mmol) were added thereto in turn. The reaction system was replaced with nitrogen for three times, and then 1,1-bis(diphenylphosphino)ferrocene palladium dichloride (94 mg, 128.73 μmol) was added thereto. The reaction solution was heated to 100° C. and continued to stir for 11 hours. The mixture was cooled, and the organic solvent was removed under reduced pressure. The obtained crude product was purified by silica gel column chromatography (eluent: 0-50% ethyl acetate/petroleum ether) to obtain compound 17. $^1$H NMR (400 MHz, CDCl$_3$): 9.11 (s, 2H), 5.24-5.05 (m, 4H), 1.37 (s, 12H).

Step 15: Synthesis of Compound 19

Compound 18 (20.00 g, 184.95 mmol) and ethyl 2-cyanopropionate (23.51 g, 184.95 mmol) were dissolved in 1,4-dioxane (40 mL), and the reaction solution was heated to 110° C. and continued to stir for 72 hours. The mixture was cooled, and the reaction solution was concentrated to about 20 mL to precipitate a solid, filtered. The filter cake was washed with ethyl acetate (30 mL), and the filter cake was collected to obtain compound 19. $^1$H NMR (400 MHz, CD$_3$OD): 7.53-7.46 (m, 2H), 7.42-7.35 (m, 3H), 1.77 (s, 3H).

Step 16: Synthesis of Compound 20

Compound 19 (10.00 g, 52.85 mmol) was dissolved in N,N-dimethylformamide (150 mL), and N,N-diisopropylethylamine (20.49 g, 158.55 mmol) and N-phenylbis(trifluoromethanesulfonyl)imide (19.82 g, 55.49 mmol) were added thereto in turn. The reaction solution was continued to stir at 25° C. for 16 hours. The reaction solution was poured into 500 mL of water, then extracted with ethyl acetate (150 mL*3), and the organic phases were combined. The organic phase was washed with brine (300 mL), dried with anhydrous sodium sulfate, filtered, and the filtrate was concentrated to dryness to obtain a crude product of compound 20. $^1$H NMR (400 MHz, CDCl$_3$): 7.54-7.44 (m, 4H), 7.40-7.34 (m, 1H), 3.76 (s, 2H), 1.95 (s, 3H).

Step 17: Synthesis of Compound 21

Compound 20 (320 mg, 1.14 mmol) was dissolved in a mixed solution of dioxane (2.5 mL) and water (0.5 mL), and compound 17 (293 mg, 912.00 μmol) and 1,1-bis(diphenylphosphino)ferrocene palladium dichloride (83 mg, 114.00 μmol) were added thereto, and finally sodium carbonate (242 mg, 2.28 mmol) was added thereto. The reaction system was replaced with nitrogen three times. The reaction solution was heated to 100° C. and stirred for 14 hours. The reaction solution was dried with anhydrous sodium sulfate, filtered and concentrated. The crude product was purified by column chromatography (eluent: 0-25% ethyl acetate/petroleum ether) to obtain compound 21. $^1$H NMR (400 MHz, CDCl$_3$): 9.11 (s, 2H), 7.64-7.27 (m, 5H), 5.32-4.88 (m, 4H), 3.67 (s, 2H), 2.10 (s, 3H).

Step 18: Synthesis of the Compound of Formula (I)

Compound 21 (60 mg, 184.42 μmol) was dissolved in dichloromethane (5 mL), and triphosgene (43.78 mg, 147.54 μmol) and N,N-diisopropylethylamine (71.50 mg, 553.27 μmol, 96.37 μL) were added thereto. The reaction solution was stirred at 20° C. for 20 minutes. Compound 13 (139.72 mg, 184.42 μmol) and N,N-diisopropylethylamine (71.50 mg, 553.27 μmol, 96.37 μL) were added thereto, and the reaction solution was continued to stir at 20° C. for 15 hours. The organic solvent was removed under reduced pressure, and the obtained crude product was purified by high performance liquid chromatography (chromatographic column: Xtimate C18 150*25 mm*5 μm; mobile phase: [water (10 mM ammonium bicarbonate)-acetonitrile]; acetonitrile %: 37%-58%, 10.5 min) to obtain the compound of formula (I). $^1$H NMR (400 MHz, CD$_3$OD): 9.28 (s, 2H), 7.67-7.40 (m, 5H), 6.66-6.49 (m, 2H), 5.84 (s, 1H), 5.33-5.20 (m, 2H), 5.14-5.00 (m, 2H), 4.34-4.16 (m, 2H), 3.53 (t, J=5.2 Hz, 2H), 3.37 (s, 3H), 3.17-3.05 (m, 2H), 2.87-2.78 (m, 1H), 2.79-2.63 (m, 2H), 2.58-2.47 (m, 1H), 2.23 (s, 3H); MS m/z=579.4 [M+1]$^+$.

Embodiment 2: Preparation of the Crystal Form A of the Compound of Formula (I)

50 mg of the compound of formula (I) was added into a 4.0 mL glass vial, and 1 mL of water was added thereto to make the mixture into a suspension. After a magneton was added, a sample of the above suspension was placed on a magnetic heating stirrer (50° C.) for testing, stirred at 50° C. for 48 hours, and then centrifuged. The residue was placed in a vacuum drying oven (60° C.) to dry overnight to obtain the crystal form A of the compound of formula (I).

50 mg of the compound of formula (I) was added into a 4.0 mL glass vial, and 1 mL of a mixed solvent of acetone and water (1:4) was added thereto to make the mixture into a suspension. After the magneton was added, a sample of the above suspension was placed on the magnetic heating stirrer (50° C.) for testing, stirred at 20° C. for 96 hours, and then centrifuged. The residue was placed in the vacuum drying oven (60° C.) to dry overnight to obtain the crystal form A of the compound of formula (I).

Embodiment 3: Preparation of the Crystal Form B of the Compound of Formula (I)

50 mg of the compound of formula (I) was weighted and added into a 4.0 mL glass vial, and 1 mL of ethanol was added thereto to make the mixture into a suspension. After the magneton was added, a sample of the above suspension was placed on the magnetic heating stirrer (50° C.) for testing. After stirring at 50° C. for 48 hours, the solution was clarified. After the solvent was volatilized, the residue was placed in the vacuum drying oven (60° C.) to dry overnight to obtain the crystal form B of the compound of formula (I).

50 mg of the compound of formula (I) was weighted and added into a 4.0 mL glass vial, and 1 mL of acetonitrile was added thereto to make the mixture into a suspension. After the magneton was added, a sample of the above suspension was placed on the magnetic heating stirrer (20° C.) for testing. After stirring at 20° C. overnight, the solution was clarified. After the solvent was volatilized, the residue was placed in the vacuum drying oven (60° C.) to dry overnight to obtain the crystal form B of the compound of formula (I).

Embodiment 4: Preparation of the Crystal Form C of the Compound of Formula (I)

50 mg of the compound of formula (I) was weighted and added into a 4.0 mL glass vial, and 1 mL of ethyl acetate was added thereto to make the mixture into a suspension. After the magneton was added, a sample of the above suspension was placed on the magnetic heating stirrer (50° C.) for testing. After stirring at 50° C. for 48 hours, the solution was clarified. Half of the solution was taken and added with 20 mg of the compound of formula (I), stirred at 20° C. for 48 hours, and then centrifuged. The residue was placed in the vacuum drying oven (60° C.) to dry overnight to obtain the crystal form C of the compound of formula (I).

Embodiment 5: Preparation of the Crystal Form D of the Compound of Formula (I)

50 mg of the compound of formula (I) was weighted and added into a 4.0 mL glass vial, and 1 mL of ethyl acetate was added thereto to make the mixture into a suspension. After the magneton was added, a sample of the above suspension was placed on the magnetic heating stirrer (50° C.) for testing. After stirring at 50° C. for 48 hours, the solution was clarified. After the solvent was volatilized, the residue was placed in the vacuum drying oven (60° C.) to dry overnight to obtain the crystal form D of the compound of formula (I).

Embodiment 6: Preparation of the Crystal Form E of the Compound of Formula (I)

50 mg of the compound of formula (I) was added into a 4.0 mL glass vial, and 1 mL of a mixed solvent of methanol and water (1:1) was added thereto to make the mixture into a suspension. After the magneton was added, a sample of the above suspension was placed on the magnetic heating stirrer (50° C.) for testing, stirred at 50° C. for 48 hours, and then centrifuged. The residue was placed in the vacuum drying oven (60° C.) to dry overnight to obtain the crystal form E of the compound of formula (I).

50 mg of the compound of formula (I) was added into a 4.0 mL glass vial, and 1 mL of methanol was added thereto to make the mixture into a suspension. After the magneton was added, a sample of the above suspension was placed on the magnetic heating stirrer (20° C.) for testing, stirred at 20° C. for 96 hours, and then centrifuged. The residue was placed in the vacuum drying oven (60° C.) to dry overnight to obtain the crystal form E of the compound of formula (I).

50 mg of the compound of formula (I) was added into a 4.0 mL glass vial, and 1 mL of a mixed solvent of acetonitrile and water (1:1) was added thereto to make the mixture into a suspension. After the magneton was added, a sample of the above suspension was placed on the magnetic heating stirrer (20° C.) for testing, stirred at 20° C. for 96 hours, and then centrifuged. The residue was placed in the vacuum drying oven (60° C.) to dry overnight to obtain the crystal form E of the compound of formula (I).

50 mg of the compound of formula (I) was added into a 4.0 mL glass vial, and 1 mL of ethanol was added thereto to make the mixture into a suspension. After the magneton was added, a sample of the above suspension was placed on the magnetic heating stirrer (50° C.) for testing. After stirring at 50° C. for 48 hours, the solution was clarified. Half of the solution was taken and added with 20 mg of the compound of formula (I), stirred at 20° C. for 48 hours, and then centrifuged. The residue was placed in the vacuum drying oven (60° C.) to dry overnight to obtain the crystal form E of the compound of formula (I).

100 mg of the compound of formula (I) was added into a 4.0 mL glass vial, and 1 mL of a mixed solvent of ethanol and water (1:4) was added thereto to make the mixture into a suspension. After the magneton was added, a sample of the above suspension was placed on the magnetic heating stirrer (40° C.) for testing, stirred at 40° C. for 60 hours, and then centrifuged. The residue was placed in the vacuum drying oven (60° C.) to dry overnight to obtain the crystal form E of the compound of formula (I).

Embodiment 7: Preparation of the Crystal Form F of the Compound of Formula (I)

17 g of the compound of formula (I) was added into a 1 L glass bottle, and 200 mL of a mixed solvent of ethanol and water (1:4) was added thereto to make the mixture into a suspension. A sample of the above suspension was placed on the magnetic heating stirrer (50° C.) for testing, stirred at 50° C. for 24 hours, and then filtered. The filter cake was collected, and the obtained sample was placed in the vacuum drying oven (60° C.) to dry overnight after repeating the above operation for 5 times to obtain the crystal form F of the compound of formula (I).

Embodiment 8: Solid Stability Test of the Crystal Form E of the Compound of Formula (I)

According to the "Guidelines for the Stability Test of APIs and Preparations" (Chinese Pharmacopoeia 2015 Edition Part IV general rules 9001), the stability of the crystal form E of the compound of formula (I) was investigated at high temperature (60° C., opened), high humidity (room temperature/relative humidity 92.5%, opened) and strong illumination (5000 1x, closed).

10 parts of the crystal form E of the compound of formula (I) were weighed in parallel, each of which was about 15 mg, and placed at the bottom of a glass sample bottle to spread into a thin layer. The 10 parts of the crystal form E were placed under conditions of high temperature (60° C.), high humidity (92.5% humidity, room temperature), high temperature and high humidity (60° C./75% humidity, 60° C./75% humidity) and stable illumination, respectively. Samples placed under high temperature and high humidity conditions were sealed with aluminum foil paper and small holes were punched in the aluminum foil paper to ensure that the sample could fully contact with ambient air; samples placed under strong illumination conditions were sealed with threaded caps. Samples placed under high temperature (60° C.) and high humidity (92.5% humidity, room temperature) conditions were sampled and tested (XRPD and purity) on the 5th and 10th day. Samples placed under the high temperature and high humidity (60° C./75% humidity, 60° C./75% humidity) were sampled and tested (XRPD and purity) on the 30th and 60th days. Samples placed under the condition of illumination were sampled and tested when the total illuminance reached $1.2 \times 10^6$ Lux·hr. The test results were compared with the initial test results of 0 day, and the test results were shown in Table 7 below:

TABLE 7

Solid stability test results of the crystal form E of the compound of formula (I)

| Test condition | Time point | Crystal form | Purity (%) |
|---|---|---|---|
| — | 0 day | Crystal form E | 98.75% |
| High temperature (60° C., opened) | 5 days | Crystal form E | 98.74% |
|  | 10 days | Crystal form E | 98.74% |
| High humidity (room temperature/relative humidity 92.5%, opened) | 5 days | Crystal form E | 98.62% |
|  | 10 days | Crystal form E | 98.72% |
| Illumination (total illuminance 1.2 × 10⁶ Lux · hr/near ultraviolet 200 w · hr/m², opened) | — | Crystal form E | 98.83% |
| 40° C., relative humidity 75%, opened | 30 days | Crystal form E | 98.14% |
|  | 60 days | Crystal form E | 98.06% |
| 60° C., relative humidity 75%, opened | 30 days | Crystal form E | 98.17% |
|  | 60 days | Crystal form E | 98.22% |

Conclusion: The crystal form E of the compound of formula (I) has good stability under the conditions of high temperature, high humidity, strong illumination and accelerated conditions.

Embodiment 9: Study on the Hygroscopicity of the Crystal Form E of the Compound of Formula (I)

Figure 19:
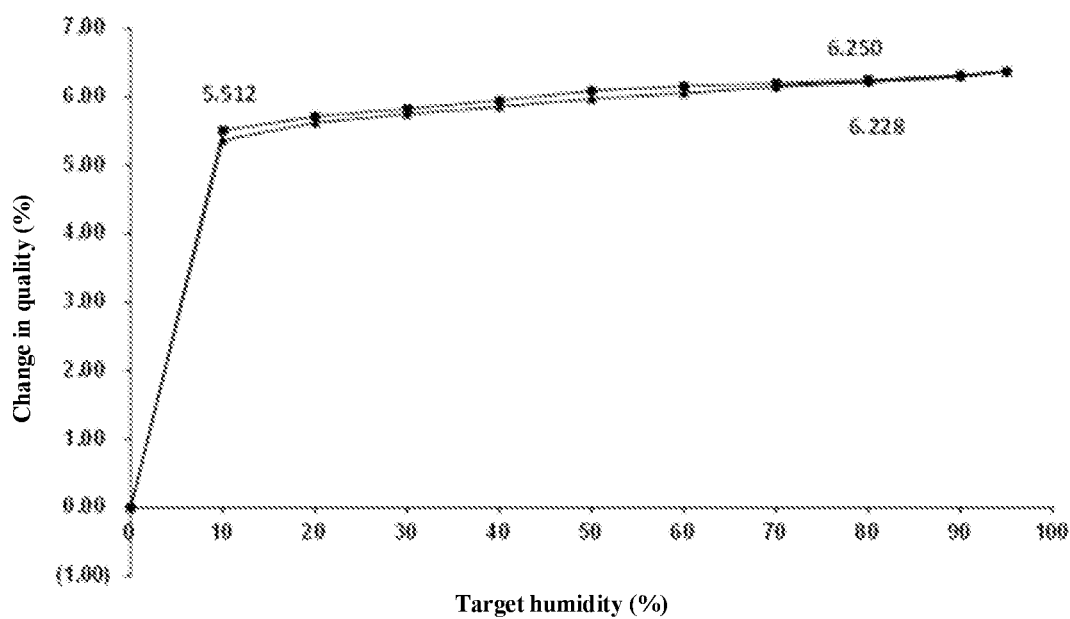
FIG. 19 is the DVS pattern of the crystal form E of the compound of formula (I).
Figure 20:
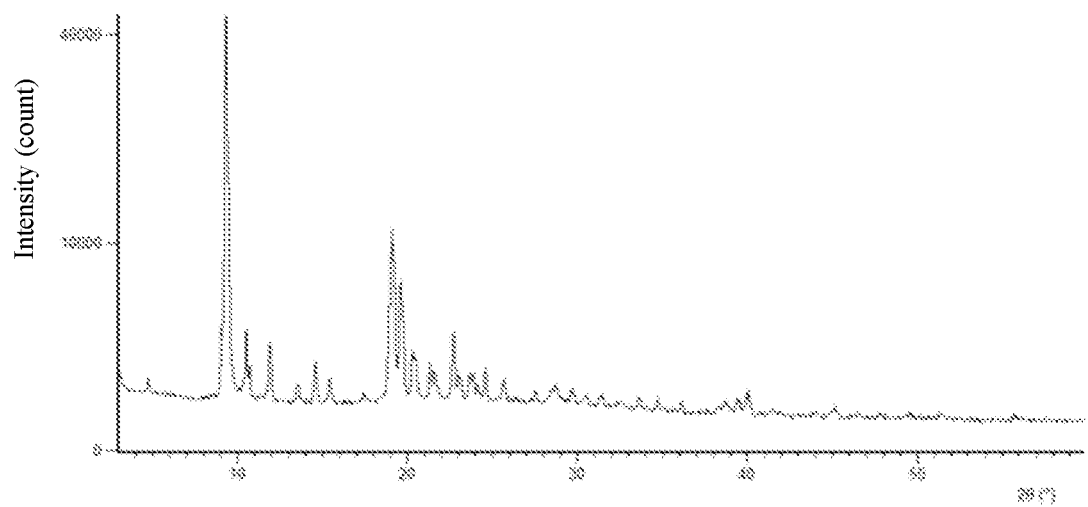
FIG. 20 is the XRPD pattern of the crystal of the compound of formula (II) measured by Cu-Kα radiation.

Experimental Materials:
Intrinsic dynamic vapor sorption instrument
Experimental Method:
10 to 15 mg of the crystal form E of the compound of formula (I) was placed in a DVS sample tray for testing.
Experimental Results:
The DVS pattern of the crystal form E of the compound of formula (II) was shown in the FIG. 19, where ΔW=6.228%.
Experimental Conclusion:
The hygroscopic weight gain of the crystal form E of the compound of formula (I) at 25° C. and 80% RH was 6.228%, which was hygroscopic.

Experimental Embodiment 1: TrkA Enzyme Activity Test

Experimental Materials
TrkA Invitrogen-PV4114
TK detection kit Cisbio-62TK0PEJ
Test plate PerkinElmer-6007299
Envision PerkinElmer-2104
Kinase Reaction Buffer
50 mM Hepes (pH 7.5), 5 mM $MgCl_2$ (magnesium chloride), 0.01 mM orthovanadate (sodium vanadate), 1% BSA (bovine serum albumin), 1 mM (dithiothreitol)
Experimental Method:
This experiment used Cisbio's homogeneous time-resolved fluorescence resonance energy transfer (HTRF® method) for activity test. In the test plate, the enzyme, biotin-labeled peptide substrate, ATP, and test compound were mixed, and incubated for reaction. After the reaction, ethylenediaminetetraacetic acid was added to terminate the reaction; at the same time, Eu-labeled antibody and streptavidin-labeled XL665 were added for reaction and detection. The data were expressed by the readings of the fluorescence signal at 665 nm and 620 nm, where a high ratio of 665 nm/620 nm indicated higher activity, and a low ratio of 665 nm/620 nm indicated inhibition of activity.

Experimental Procedures
1. Dilution of compound: the test compound was 3-fold diluted to prepare a total of 11 concentrations, the concentration was from 10 μM to 0.17 nM in the final system;
2. A 10 μL reaction system with a buffer of 50 mM Hepes (pH 7.5), 5 mM $MgCl_2$, 0.01 mM sodium vanadate, 1% BSA, and 1 mM DTT, and containing 0.5 nM TrkA kinase, 0.3 μM biotin-TK peptide (biotin-labeled tyrosine kinase substrate peptide), 90 μM ATP was incubated at 23° C. for 90 minutes. 10 μL of stop solution containing 20 mM EDTA, 1.34 nM phosphorylated substrate antibody, and 100 nM streptavidin-labeled fluorescent molecule XL-665 was then added, incubated at 23° C. for 60 minutes; the signal was read with Envision;
3. The inhibition rate of the compound was calculated from the data read by the instrument, and the $IC_{50}$ value was calculated using the mode 205 in XLFIT5 of IDBS.
Experimental Results
The results are shown in Table 8.

TABLE 8

| $IC_{50}$ value of the compound of formula (I) inhibiting TrkA enzyme | |
|---|---|
| Number of the compound | TrkA $IC_{50}$ (nM) |
| Compound of formula (I) | 0.56 |

The results show that the compound of formula (I) has a significant inhibitory effect on TrkA enzyme.

Experimental Embodiment 2: Plasma Protein Binding Rate (PPB) Test

Experimental Objective
The protein binding rates of the test compound in the plasma of humans and SD rats were determined.
Experimental Operation
796 μL of blank plasma from humans and SD rats (plasma purchased from BioreclamationIVT) were taken, 4 μL of working solution of the test compound (400 μM) or warfarin working solution (400 μM) was added and the final concentration of the test compound or warfarin was 2 μM. The sample was mixed thoroughly. The final concentration of organic phase DMSO was 0.5%; 50 μL of the plasma sample treated with the test compound or warfarin was pipetted into the sample receiving plate, and a corresponding volume of blank plasma or buffer was added immediately so that the final volume in each sample well was 100 μL, the volume ratio of plasma: dialysis buffer was 1:1; 400 μL of stop solution was added to these samples, and these samples were used as To samples for recovery and stability determination. To samples were stored at 2° C. to 8° C. for subsequent processing together with other dialyzed samples; 150 μL of the plasma sample treated with the test compound or warfarin was added into the dosing end of each dialysis hole, and 150 μL of blank dialysis buffer was added to the receiving end corresponding to the dialysis hole. Then the dialysis plate was sealed with gas-permeable membrane and placed in a humidified 5% $CO_2$ incubator, and incubated at 37° C. with 100 rpm shaking for 4 hours. After the dialysis, 50 μL of the dialysis buffer sample and the dialysis plasma sample were transferred to a new sample receiving plate. A corresponding volume of blank plasma or buffer was added to the sample, so that the final volume was 100 μL in each sample well, and the volume ratio of plasma:dialysis buffer was 1:1. All samples were analyzed by LC/MS/MS after protein precipitation, and the plasma protein unbound rate, binding rate and recovery rate was calculated according to the following formula: % unbound rate=100*free compound concentration at the membrane buffer side/total compound concentration at the membrane plasma side, % protein binding rate=100−% unbound rate, % recovery rate=100* (free compound concentration at the membrane buffer side+ total compound concentration at the membrane plasma side)/total compound concentration before dialysis.

Experimental Results

The results are shown in Table 9.

TABLE 9

Human and rat plasma protein unbound rates of the compound of formula (I)

| | Plasma protein unbound rate | |
|---|---|---|
| Number of the compound | Human plasma | SD rat plasma |
| Compound of formula (I) | 13.2% | 7.1% |

The results show that the compound of formula (I) has a high plasma protein unbound rate.

Experimental Embodiment 3: Cytochrome P450 Isozyme Inhibitory Activity Test

Experimental Objective

The inhibitory activities of the test compound on different subtypes of human cytochrome P450 isozymes were determined.

Experimental Operation

The test compound, standard inhibitor (100× final concentration), and a mixed substrate working solution were prepared; the microsome frozen in −80° C. refrigerator was thawed. 2 μL of the test compound and standard inhibitor solution were added to the corresponding wells, and at the same time 2 μL of the corresponding solvent was added to the non-inhibitor control wells (NIC) and blank control wells (Blank) wells; then 20 μL of mixed substrate solution was added to the corresponding wells, except for the Blank wells (20 μL of PB was added to the Blank wells); a human liver microsome solution was prepared (put back into the refrigerator immediately after using and marking the date), and then 158 μL of the human liver microsome solution was added to all wells; the above sample plate was placed in a 37° C. water bath for pre-incubation, then the coenzyme factor (NADPH) solution was prepared; 10 minutes later, 20 μL of the NADPH solution was added to all wells, and the sample plate was shaken well, placed in a 37° C. water bath and incubated for 10 minutes; at the corresponding time point, 400 μL of cold acetonitrile solution (internal standard: 200 ng/mL tolbutamide and labetalol) was added to terminate the reaction; the sample plate was evenly mixed, centrifuged at 4000 rpm for 20 minutes to precipitate proteins; 200 μL of the supernatant was added to 100 μL of water, shook well, and tested by LC/MS/MS.

Experimental Results

The results are shown in Table 10.

TABLE 10

IC$_{50}$ value of the compound of formula (I) for P450 isozyme inhibition

| | Cytochrome P450 isozyme IC$_{50}$ (nM) | | | | |
|---|---|---|---|---|---|
| Number of the compound | CYP1A2 | CYP2C9 | CYP2C19 | CYP2D6 | CYP3A4 |
| Compound of formula (I) | >50 | 39.1 | >50 | 40.6 | >50 |

The results show that the compound of formula (I) has a low risk of drug-drug interaction.

Experimental Embodiment 4: Metabolic Stability (MMS) Study in Liver Microsomes

Experimental Objective

The metabolic stability of the test compound in human and rat liver microsomes was tested.

Experimental Materials

Test compound (10 mM), Testosterone (reference compound, 10 mM), Diclofenac (reference compound, 10 mM) and Propafenone (reference compound, 10 mM).

Buffer System 1. 100 mM potassium phosphate buffer (pH 7.4).
2. 10 mM MgCl$_2$.

Dilution of Compound

1. Intermediate solution: 45 μL of DMSO (with 450 μL of 1:1 methanol/water) was used to dilute 5 μL of the sample for test compound or reference compound.
2. Working solution: 450 μL of 100 mM potassium phosphate buffer was used to dilute the intermediate solution.

NADPH Regeneration System

1. β-Phosphoramidate adenine dinucleotide, from Sigma, Cat. No. N0505.
2. Isocitric acid, from Sigma, Cat. No. 11252.
3. Isocitrate dehydrogenase, from Sigma, Cat. No. 12002.

| Preparation of a liver microsome solution (final concentration: 0.5 mg protein/mL) | | |
|---|---|---|
| Microsomes | Product information | Source |
| Human liver microsomes | Cat No. 452117 Lot No. 38291 | BD Biosciences |
| Rat liver microsomes | Cat No. R1000 Lot No. 1310030 | Xenotech |
| Canine liver microsomes | Cat No. D1000 Lot No. 1310086 | Xenotech |

Stop Solution

Cold acetonitrile containing 100 ng/mL tolbutamide and 100 ng/mL labetalol was used as the internal standard.

Experimental Method

10 μL of the working solution of the test compound or reference compound was added to all plates (T$_0$, T$_5$, T$_{10}$, T$_{20}$, T$_{30}$, T$_{60}$, and NCF$_{60}$).

680 μL of liver microsome solution was added to each well of 96-well plates, then 80 μL was added to each well of the plates, and the plates were placed at 37° C. for pre-incubation for approximately 10 minutes.

10 μL of 100 mM potassium phosphate buffer was added to each well of the NCF$_{60}$ plate.

After the pre-incubation, 90 μL NADPH regeneration system working solution was added to each well of the 96-well plates, and then 10 μL was added to each well of the plates to initiate the reaction.

Incubation for an appropriate time (such as 5, 10, 20, 30, and 60 minutes).

300 μL of the stop solution (refrigerated at 4° C., containing 100 ng/mL tolbutamide and 100 ng/mL labetalol) was added into each sample well.

The sample plate was shaken for about 10 minutes and centrifuged at 4000 rpm for 20 minutes at 4° C.

During centrifugation, 300 μL of HPLC water was added to each well, and 100 μL of the supernatant was collected for LC-MS/MS analysis.

Data Analysis

The half-life $T_{1/2}$ and the intrinsic clearance rate by liver microsome $C_{lint(mic)}$ were calculated by the following formulas:

$$C_t = C_{ij} \cdot e^{-ks \cdot i}$$

when $$C_t = \frac{1}{2}C_0,$$

$$T_{1/2} = \frac{Ln2}{k_e} = \frac{0.693}{k_e}$$

$$CL_{int(mic)} = \frac{0.693}{T_{1/2}} \cdot \frac{1}{\text{Concentration of microsomal protein during incubation (mg/mL)}}$$

$$CL_{int(liver)} = CL_{int(mic)} \cdot \frac{\text{Microsomal protein(mg)}}{\text{Liverweight(g)}} \cdot \frac{\text{Liverweight(g)}}{\text{Bodyweight(kg)}}$$

$$C_t = C_{ij} \cdot e^{-ks \cdot i}$$

when $$C_t = \frac{1}{2}C_0,$$

$$T_{1/2} = \frac{Ln2}{k_e} = \frac{0.693}{k_e}$$

$$CL_{int(mic)} = \frac{0.693}{T_{1/2}} \cdot \frac{1}{\text{Concentration of microsomal protein during incubation (mg/mL)}}$$

$$CL_{int(liver)} = CL_{int(mic)} \cdot \frac{\text{Microsomal protein(mg)}}{\text{Liverweight(g)}} \cdot \frac{\text{Liverweight(g)}}{\text{Bodyweight(kg)}}$$

Each gram of liver contained 45 mg of microsomal protein, and the liver weights of mice, rats, dogs, monkeys and humans were 88 g/kg, 40 g/kg, 32 g/kg, 30 g/kg and 20 g/kg, respectively.

$C_t$ is the concentration at time t, t is the incubation time, $C_0$ is the concentration at 0, $k_e$ is the elimination rate constant, $Cl_{int(mic)}$ is the intrinsic clearance rate by liver microsome, and $Cl_{int(liver)}$ is the intrinsic clearance rate by liver.

Experimental Results

The results are shown in Table 11.

TABLE 11

| Clearance rate of the compound of formula (I) in human and rat liver microsomes | | |
|---|---|---|
| | Intrinsic clearance rate of liver microsomes (mL/min/Kg) | |
| Number of the compound | Human | Rat |
| Compound of formula (I) | 51.7 | 24.9 |

The results show that the compound of formula (I) has good metabolic stability of liver microsomes in two species of human and rat.

Experimental Embodiment 5: In Vivo Pharmacokinetic Study of the Crystal Form E of the Compound of Formula (I) in Rats After Single Administration Experimental Objective Male SD rats were used as test animals, and the concentration of the compound in blood was determined after single administration to evaluate the pharmacokinetic behavior.

Experimental Materials:

Sprague Dawley rats (male, 200-300 g, 7-9 weeks, Shanghai Charles River Laboratory Animal Co., Ltd.)

Experimental Operation:

The pharmacokinetic characteristics of the test compound in rodents after intravenous injection and oral administration were tested by standard protocols, in the experiment, the test compound was prepared into a clear solution or homogeneous suspension, and administered to the rats by single intravenous injection and oral administration. In the intravenous injection group, the menstruum was a certain proportion of ethanol and physiological saline solution or a certain proportion of dimethyl sulfoxide in HP-β cyclodextrin solution (the pH was adjusted to 3-4), the mixture was vortexed and stirred to prepare 1 mg/mL clear solution, then filtered with microporous membrane for later use; in the oral administration group, the menstruum was a certain proportion of sodium carboxymethyl cellulose solution or a certain proportion of dimethyl sulfoxide in HP-β cyclodextrin solution (the pH was adjusted to about 4), after the test compound was mixed with the solvent, the mixture was vortexed and stirred to prepare 30 mg/mL homogeneous suspension for later use. After 2 mg/kg intravenous administration or 300 mg/kg oral administration to rats, a certain amount of whole blood samples were collected, centrifuged at 3000 g for 15 minutes, the supernatant was separated to obtain the plasma samples; then an acetonitrile solution containing internal standard with a volume 3 times that of the plasma sample was added to precipitate proteins, and then centrifuged; the supernatant was separated, and water with a volume twice that of the supernatant was added to the supernatant, which was then centrifuged again; the supernatant was collected for analysis; LC-MS/MS analysis method was used to quantitatively analyze the blood drug concentration, and Phoenix WinNonlin software (Pharsight, USA) was used to calculate the pharmacokinetic parameters, such as peak concentration, time to peak concentration, clearance rate, half-life, area under the concentration-time curve, bioavailability, etc.

Experimental Results:

TABLE 12

Oral pharmacokinetic properties of the crystal form E of the compound of formula (I) in rats

| Test compound | | | | |
|---|---|---|---|---|
| Compound of formula (I) | 2 mpk intravenous injection | $C_0$ (nM) | | 5385 |
| | | $T_{1/2}$ (hr) | | 0.55 |
| | | $Vd_{ss}$ (L/kg) | | 0.81 |
| | | Cl (mL/min/kg) | | 22.4 |
| | | $AUC_{0-inf}$ (nM · hr) | | 2611 |
| Crystal form E of the compound of formula (I) | 300 mpk oral administration | $C_{max}$ (nM) | | 48500 |
| | | $T_{max}$ (hr) | | 0.75 |
| | | $T_{1/2}$ (hr) | | 3.25 |
| | | $AUC_{0-inf}$ (nM · hr) | | 276267 |
| | | Bioavailability | | 70.5% |

Among them, $C_0$ is the initial concentration, $T_{1/2}$ is the elimination half-life, $V_{dss}$ is the steady-state apparent volume of distribution, Cl is the total clearance rate, $AUC_{0-inf}$ is the area under the plasma drug concentration-time curve from time 0 to infinity, $C_{max}$ is the peak concentration, $T_{max}$ is the time to peak concentration.

The results show that the crystal form E of the compound of formula (I) has good pharmacokinetic properties and oral bioavailability in rats.

Experimental Embodiment 6: In Vivo Pharmacokinetic Study in Mice After Single Administration Experimental Objective Male CD-1 mice were used as test animals, the concentration of the compound in blood was determined after single administration to evaluate the pharmacokinetic behavior.

Experimental Materials:

CD-1 mice (male, 20-40 g, 6-9 weeks, Shanghai Sippr-Bk Laboratory Animal Co., Ltd.)

Experimental Operation:

The pharmacokinetic characteristics of the test compound in rodents after intravenous injection and oral administration were tested by standard protocols, in the experiment, the test compound was prepared into a clear solution or homogeneous suspension, and administered to the mice by single intravenous injection and oral administration. In the intravenous injection group, the menstruum was a certain proportion of ethanol, Cremophor EL and physiological saline solution, the mixture was vortexed to prepare 1 mg/mL clear solution, then filtered with microporous membrane for later use; in the oral administration group, the menstruum was a certain proportion of methyl cellulose solution or certain proportion of methyl cellulose and Tween 80 aqueous solution, the test compound was mixed with the menstruum, and the mixture was vortexed to prepare 10 mg/mL clear or homogeneous suspension for later use. After 2 mg/kg intravenous administration or 100 mg/kg oral administration to the mice, a certain amount of whole blood samples were collected, centrifuged at 3200 g for 10 minutes, the supernatant was separated to obtain the plasma samples, and the samples were diluted multiple times with blank plasma according to actual needs. The plasma sample was added to acetonitrile solution containing the internal standard with a volume 20 times that of the plasma sample to precipitate proteins, and then centrifuged; the supernatant was separated, and water with a volume twice that of the supernatant was added to the supernatant, which was then centrifuged again; the supernatant was collected for analysis; LC-MS/MS analysis method was used to quantitatively analyze the blood drug concentration, and Phoenix WinNonlin software (Pharsight, USA) was used to calculate the pharmacokinetic parameters, such as peak concentration, time to peak concentration, clearance rate, half-life, area under the concentration-time curve, bioavailability, etc.

Experimental Results:

TABLE 13

Pharmacokinetic properties of the compound of formula (I) in mice

| Number of the compound | | Compound of formula (I) |
|---|---|---|
| 2 mpk intravenous injection | $C_0$ (nM) | 2720 |
| | $T_{1/2}$ (hr) | 0.57 |
| | $Vd_{ss}$ (L/kg) | 1.54 |
| | Cl (mL/min/kg) | 41.7 |
| | $AUC_{0-inf}$ (nM · hr) | 1438 |
| 100 mpk oral administration | $C_{max}$ (nM) | 25550 |
| | $T_{max}$ (hr) | 0.38 |
| | $T_{1/2}$ (hr) | 0.92 |
| | $AUC_{0-inf}$ (nM · hr) | 37567 |
| | Bioavailability | 52.2% |

Among them, $C_0$ is the initial concentration, $T_{1/2}$ is the elimination half-life, $V_{dss}$ is the steady-state apparent volume of distribution, Cl is the total clearance rate, $AUC_{0-inf}$ is the area under the plasma drug concentration-time curve from time 0 to infinity, $C_{max}$ is the peak concentration, $T_{max}$ is the time to peak concentration.

The results show that the compound of formula (I) of the present disclosure has good pharmacokinetic properties and oral bioavailability in mice.

Experimental Embodiment 7: In Vivo Pharmacokinetic Study of the Crystal Form E of the Compound of Formula (I) in Beagle Dogs After Single Administration Experimental Objective Male beagle dogs were used as test animals, the concentration of the compound in blood after single administration was determined to evaluate the pharmacokinetic behavior.

Experimental Materials:

Beagle dogs (Male, 6-12 kg, more than 6 months, Beijing Marshall Biotechnology Co., Ltd.).

Experimental Operation:

The objective of the test was to study the pharmacokinetic characteristics of the test compound in non-rodent after intravenous injection and oral administration. In the experiment, the test compound was prepared into a clear solution or homogeneous suspension and administered to the beagle dogs by single intravenous injection or oral administration. In the intravenous injection group, the menstruum was a certain proportion of dimethyl sulfoxide in HP-β-cyclodextrin solution or a certain proportion of ethanol, polyethylene glycol 400 and physiological saline solution, the mixture was vortexed and subjected to ultrasonic treatment to prepare 2 mg/mL clear solution, then filtered with microporous membrane for later use; in the oral administration group, the menstruum was a certain proportion of dimethyl sulfoxide in HP-β-cyclodextrin solution or a certain proportion of sodium carboxymethyl cellulose solution, the test compound was mixed with the menstruum, vortexed and subjected to ultrasonic treatment to prepare 2 mg/mL homogeneous suspension for later use. After 2 mg/kg intravenous administration or 10 mg/kg oral administration to the Beagle dogs, a certain amount of whole blood samples were collected, centrifuged at 3000 g for 10 minutes, and the supernatant was separated to obtain plasma samples; then an acetonitrile solution containing internal standard with a volume 10 times that of the plasma sample was added to precipitate proteins, and then centrifuged; the supernatant was separated for analysis; LC-MS/MS analysis method was used to quantitatively analyze the blood drug concentration, and Phoenix WinNonlin software (Pharsight, USA) was used to calculate the pharmacokinetic parameters, such as peak concentration, time to peak concentration, clearance rate, half-life, area under the concentration-time curve, bioavailability, etc.

Experimental Results:

TABLE 14

| \multicolumn{5}{c}{Pharmacokinetic properties of crystal form E of compounds of formula (I) in dogs} |
|---|---|---|---|---|
| Test compound | Compound of formula (I) | 2 mpk intravenous injection | $C_0$ (nM) | 8463 |
| | | | $T_{1/2}$ (hr) | 0.44 |
| | | | $Vd_{ss}$ (L/kg) | 0.49 |
| | | | Cl (mL/min/kg) | 12.4 |
| | | | $AUC_{0\text{-}inf}$ (nM · hr) | 4664 |
| | Crystal form E of the compound of formula (I) | 10 mpk oral administration | Cmax (nM) | 10445 |
| | | | $T_{max}$ (hr) | 0.75 |
| | | | $T_{1/2}$ (hr) | 0.95 |
| | | | $AUC_{0\text{-}inf}$ (nM · hr) | 26362 |
| | | | Bioavailability | 113% |

Among them, $C_0$ is the initial concentration, $T_{1/2}$ is the elimination half-life, $V_{dss}$ is the steady-state apparent volume of distribution, Cl is the total clearance rate, $AUC_{0\text{-}inf}$ is the area under the plasma drug concentration-time curve from time 0 to infinity, $C_{max}$ is the peak concentration, $T_{max}$ is the time to peak concentration.

The results show that: the crystal form E of the compound of formula (I) shows a super-linear increase in exposure under low-dose (10 mpk) oral administration, indicating that the compound has good oral pharmacokinetic properties and bioavailability in beagle dogs.

What is claimed is:

1. A crystal form E of a compound of formula (II), wherein the X-ray powder diffraction pattern thereof comprises characteristic diffraction peaks at the following angles of 2θ: 9.56°±0.20°, 12.08°±0.20°, 19.29°±0.20°, wherein, n is 0 or 2,

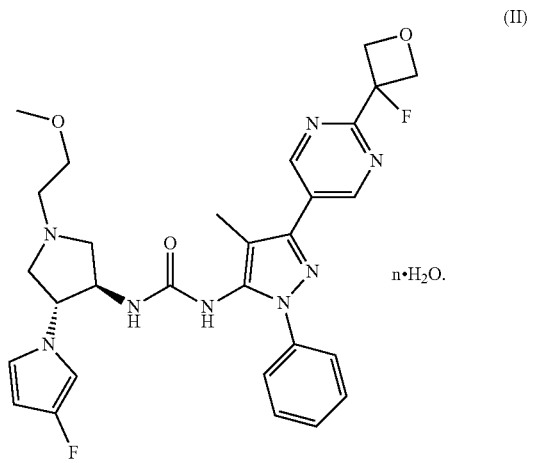 [SMILES: COCCN1C[C@@H](n2ccc(F)c2)[C@H](NC(=O)Nc2c(C)c(-c3cnc(C4(F)COC4)nc3)nn2-c2ccccc2)C1]

2. A crystal form E of a compound of formula (I), wherein the X-ray powder diffraction pattern thereof comprises characteristic diffraction peaks at the following angles of 2θ: 9.56°±0.20°, 12.08°±0.20° and 19.29°±0.20°,

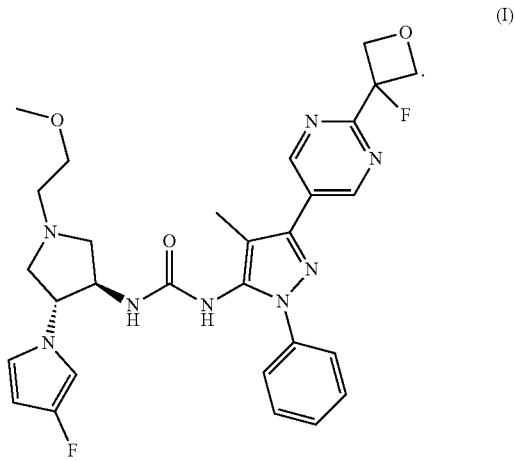 [SMILES: COCCN1C[C@@H](n2ccc(F)c2)[C@H](NC(=O)Nc2c(C)c(-c3cnc(C4(F)COC4)nc3)nn2-c2ccccc2)C1]

3. The crystal form E as claimed in claim 1, wherein the X-ray powder diffraction pattern thereof comprises characteristic diffraction peaks at the following angles of 2θ: 9.56±0.20°, 10.75±0.20°, 12.08±0.20°, 14.78±0.20°, 15.60±0.20°, 19.29±0.20°, 20.55±0.20° and 22.82±0.20°.

4. The crystal form E as claimed in claim 3, wherein the X-ray powder diffraction pattern thereof comprises characteristic diffraction peaks at the following angles of 2θ: 4.91°, 9.56°, 10.75°, 12.08°, 13.70°, 14.78°, 15.60°, 17.62°, 19.29°, 19.78°, 20.55°, 21.58°, 22.82°, 23.85°, 24.29°, 24.74°, 25.86°, 26.59°, 27.70°, 28.56°, 28.94°, 30.67°, 31.50° and 37.80°.

Figure 13:
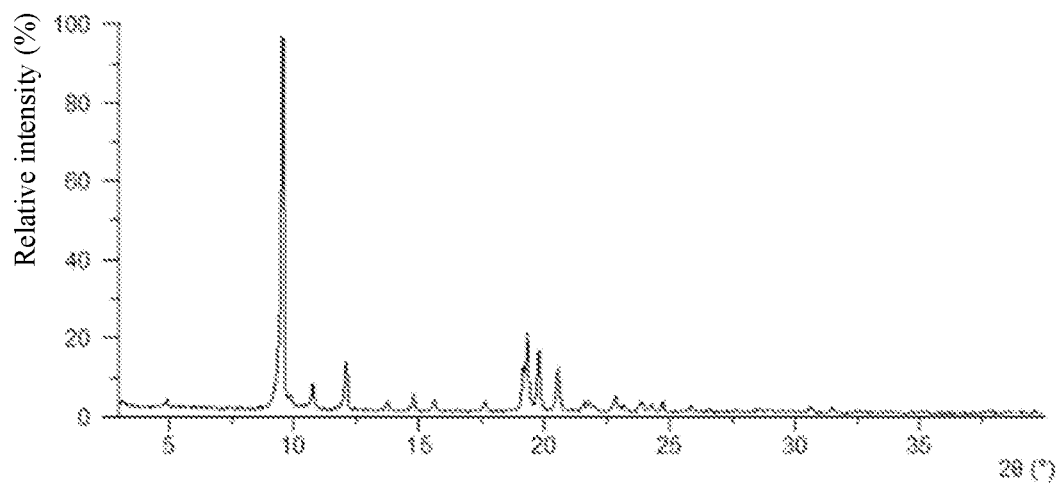
FIG. 13 is the XRPD pattern of the crystal form E of the compound of formula (I) measured by Cu-Kα radiation.

5. The crystal form E as claimed in claim 4, wherein the XRPD pattern thereof is shown in FIG. 13.

6. The crystal form E as claimed in claim 1, wherein the differential scanning calorimetry curve has an endothermic peak at 94.0±3.0° C., 154.0±3.0° C. and 171.7±3.0° C. respectively and an exothermic peak at 123.8±3.0° C.

Figure 14:
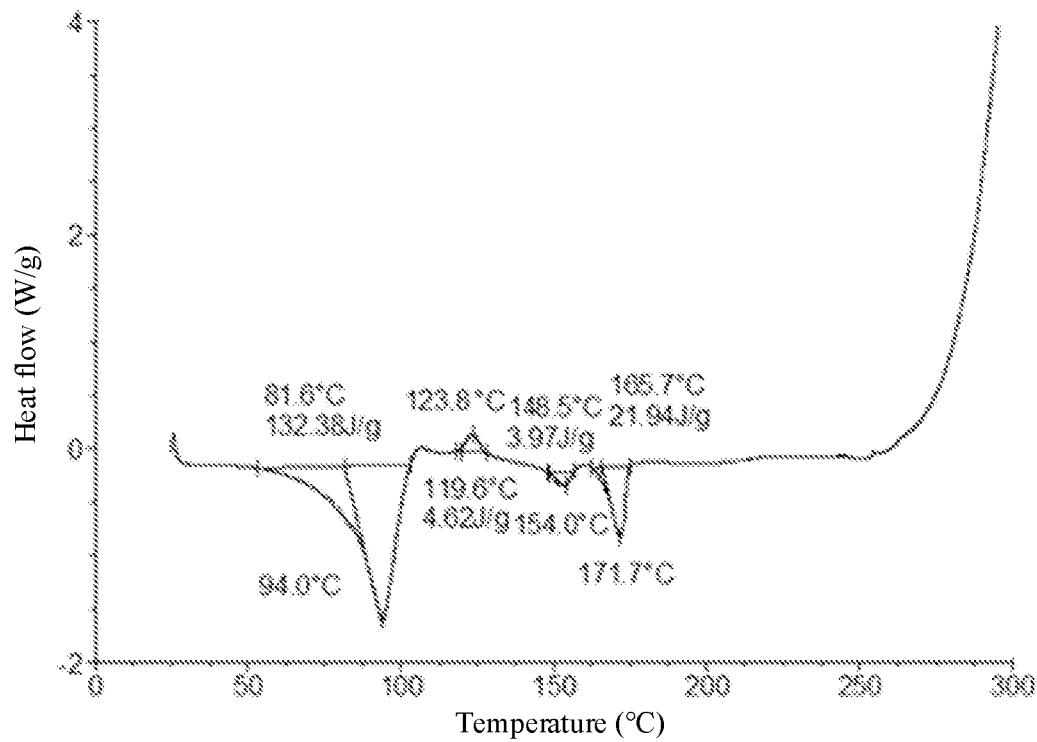
FIG. 14 is the DSC pattern of the crystal form E of the compound of formula (I).

7. The crystal form E as claimed in claim 6, wherein the DSC pattern thereof is shown in FIG. 14.

8. The crystal form E as claimed in claim 1, wherein the thermogravimetric analysis curve thereof has a weight loss of 5.84% occurred at 130.0±3° C.

Figure 15:
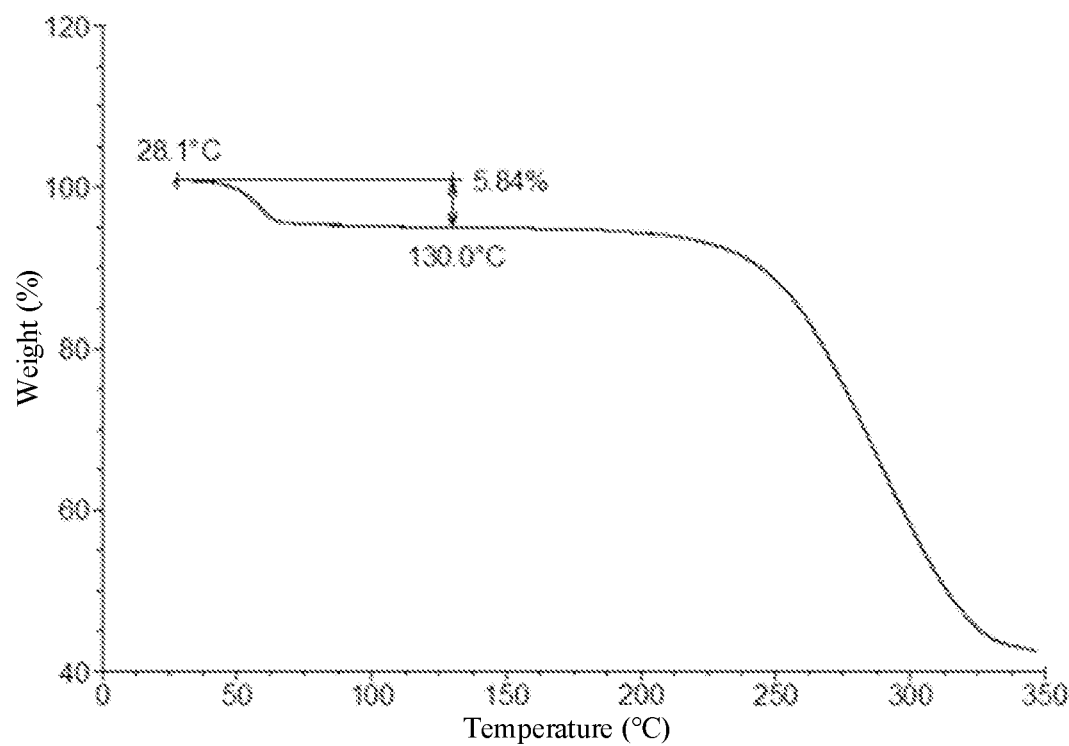
FIG. 15 is the TGA pattern of the crystal form E of the compound of formula (I).
Figure 16:
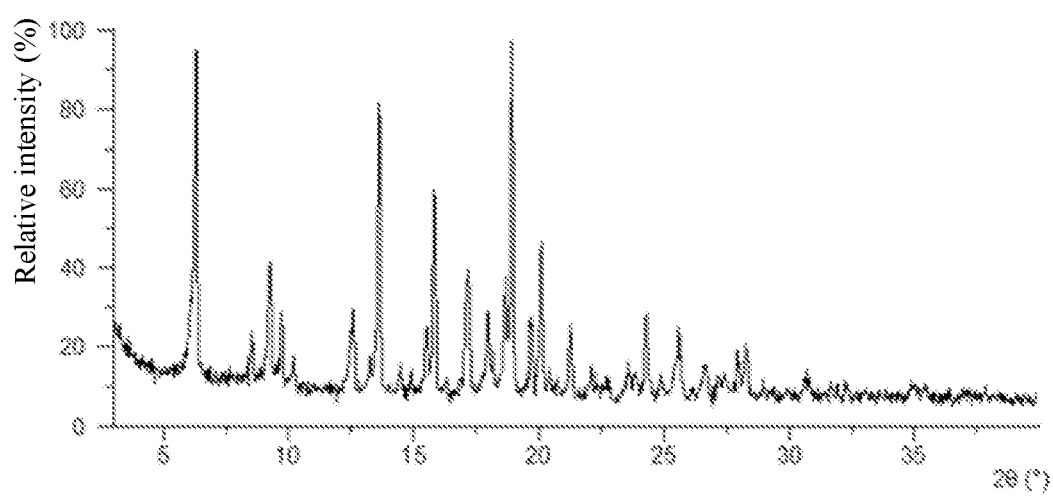
FIG. 16 is the XRPD pattern of the crystal form F of the compound of formula (I) measured by Cu-Kα radiation.
Figure 17:
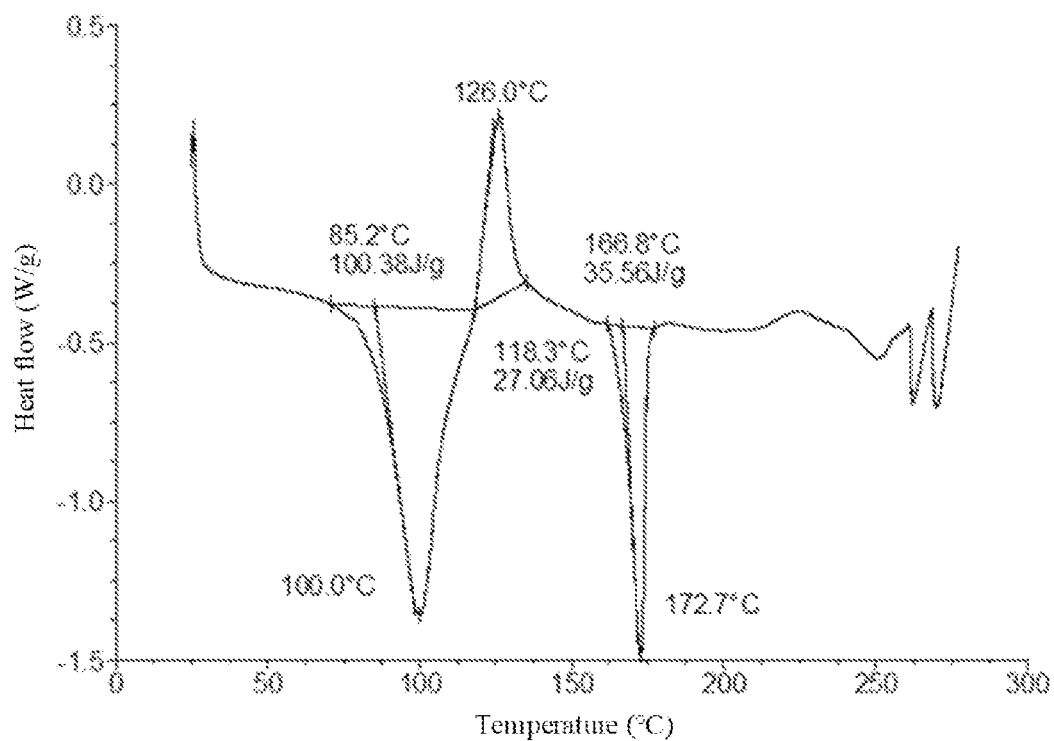
FIG. 17 is the DSC pattern of the crystal form F of the compound of formula (I).
Figure 18:
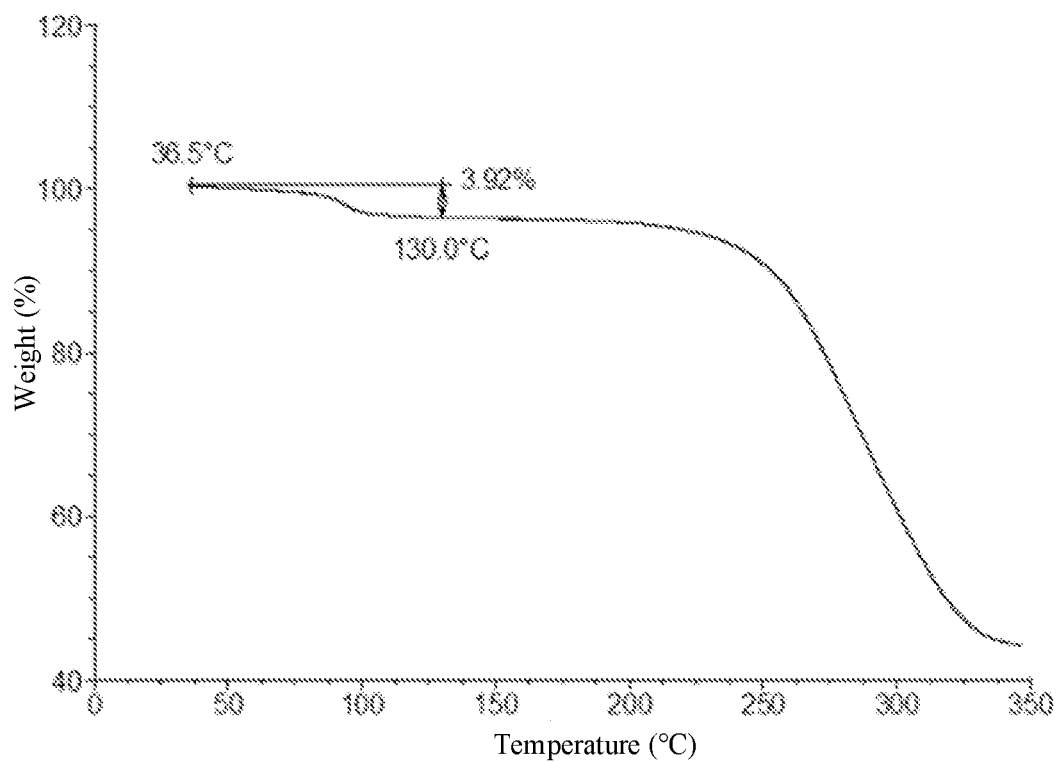
FIG. 18 is the TGA pattern of the crystal form F of the compound of formula (I).

9. The crystal form E as claimed in claim 8, wherein a TGA pattern thereof is shown in FIG. 15.

10. A preparation method for a crystal form E of a compound of formula (I), comprising adding any form of the compound of formula (I) into an alcohol solvent, a mixed solvent of the alcohol solvent and water or a mixed solvent of acetonitrile and water, stirring at a certain temperature for a certain time, then centrifuging, and drying a residue to obtain the crystal form E of the compound of formula (I):

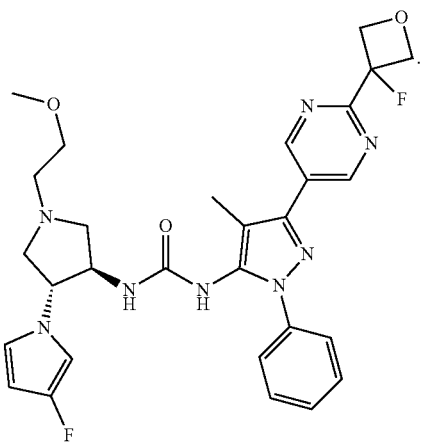
(I)

11. The preparation method as claimed in claim 10, wherein the volume ratio of the alcohol solvent to water or acetonitrile to water is selected from 1:1 to 4.

12. The preparation method as claimed in claim 10, wherein the alcohol solvent is selected from methanol and ethanol.

13. The preparation method as claimed in claim 10, wherein the temperature for the stirring is selected from 20° C. to 60° C.

14. The preparation method as claimed in claim 10, wherein the time for the stirring is selected from 48 hours to 96 hours.

15. The preparation method as claimed in claim 10, wherein the weight-to-volume (mg/mL) ratio of the compound of formula (I) to the solvent is selected from 10 to 100:1.

* * * * *